United States Patent [19]

Burke et al.

[11] 4,094,318

[45] June 13, 1978

[54] ELECTRONIC CONTROL MEANS FOR A PLURALITY OF INTRAVENOUS INFUSION SETS

[75] Inventors: George K. Burke; Robert J. LeFevre, both of Bethlehem; Robert E. Thomas, Wind Gap, all of Pa.

[73] Assignee: Burron Medical Products, Inc., Bethlehem, Pa.

[21] Appl. No.: 703,907

[22] Filed: Jul. 9, 1976

[51] Int. Cl.² .............................................. A61M 31/31
[52] U.S. Cl. ............................ 128/214 E; 128/214 C; 128/DIG. 13; 222/52
[58] Field of Search ........... 128/214 C, 214 D, 214 E, 128/214 F, DIG. 12, DIG. 13; 222/52, 77; 137/486, 487.5

[56] References Cited

U.S. PATENT DOCUMENTS

| | | | |
|---|---|---|---|
| 3,655,095 | 3/1972 | Kienitz | 128/214 E |
| 3,749,285 | 7/1973 | Latham | 128/DIG. 13 |
| 3,869,854 | 3/1975 | Church | 58/33 |
| 3,886,937 | 6/1975 | Bobo et al. | 128/214 R |
| 3,985,133 | 10/1976 | Jenkins et al. | 128/214 E |
| 4,037,598 | 7/1977 | Georgi | 128/214 E |
| 4,038,982 | 8/1977 | Burke et al. | 128/214 E |
| 4,048,474 | 9/1977 | Olesen | 235/151.34 |

Primary Examiner—Robert W. Michell
Assistant Examiner—Francis J. Jaworski
Attorney, Agent, or Firm—Shoemaker and Mattare, Ltd.

[57] ABSTRACT

Electronic control apparatus for controlling the administration of a plurality of separate fluids independently and consecutively, includes electrical circuitry connected with a plurality of valve operators to operate valves in a plurality of sets to control flow therethrough.

23 Claims, 17 Drawing Figures

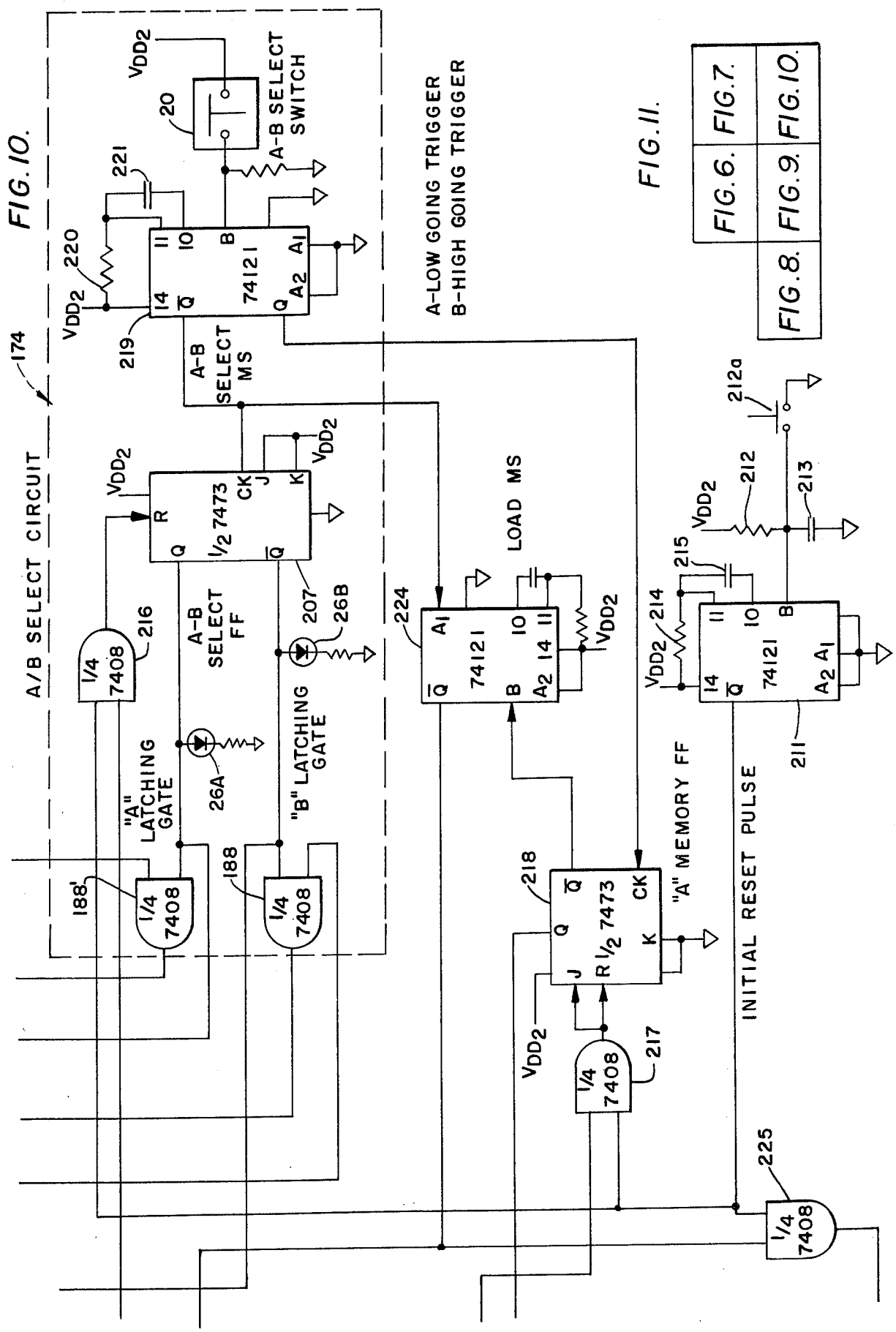

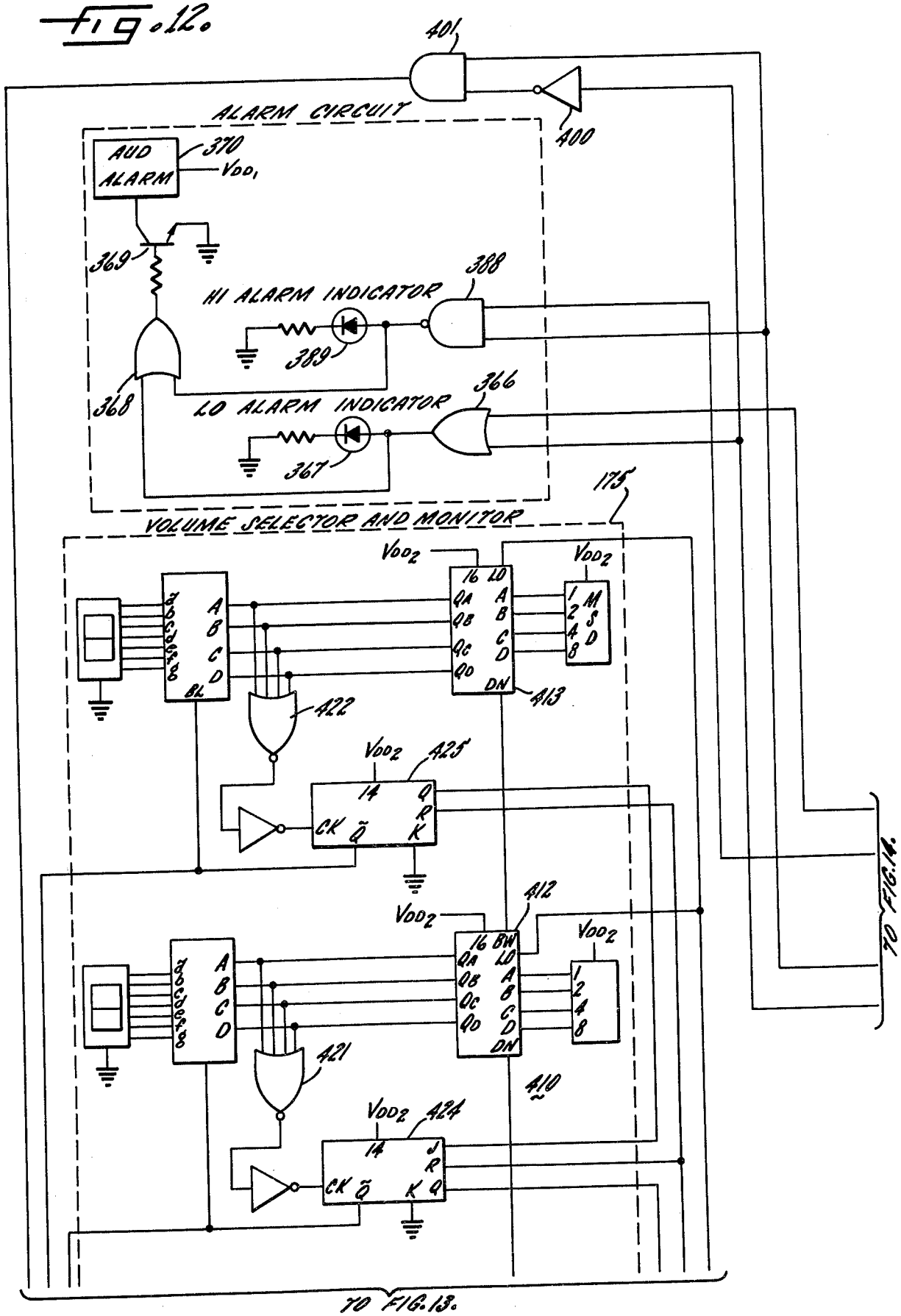

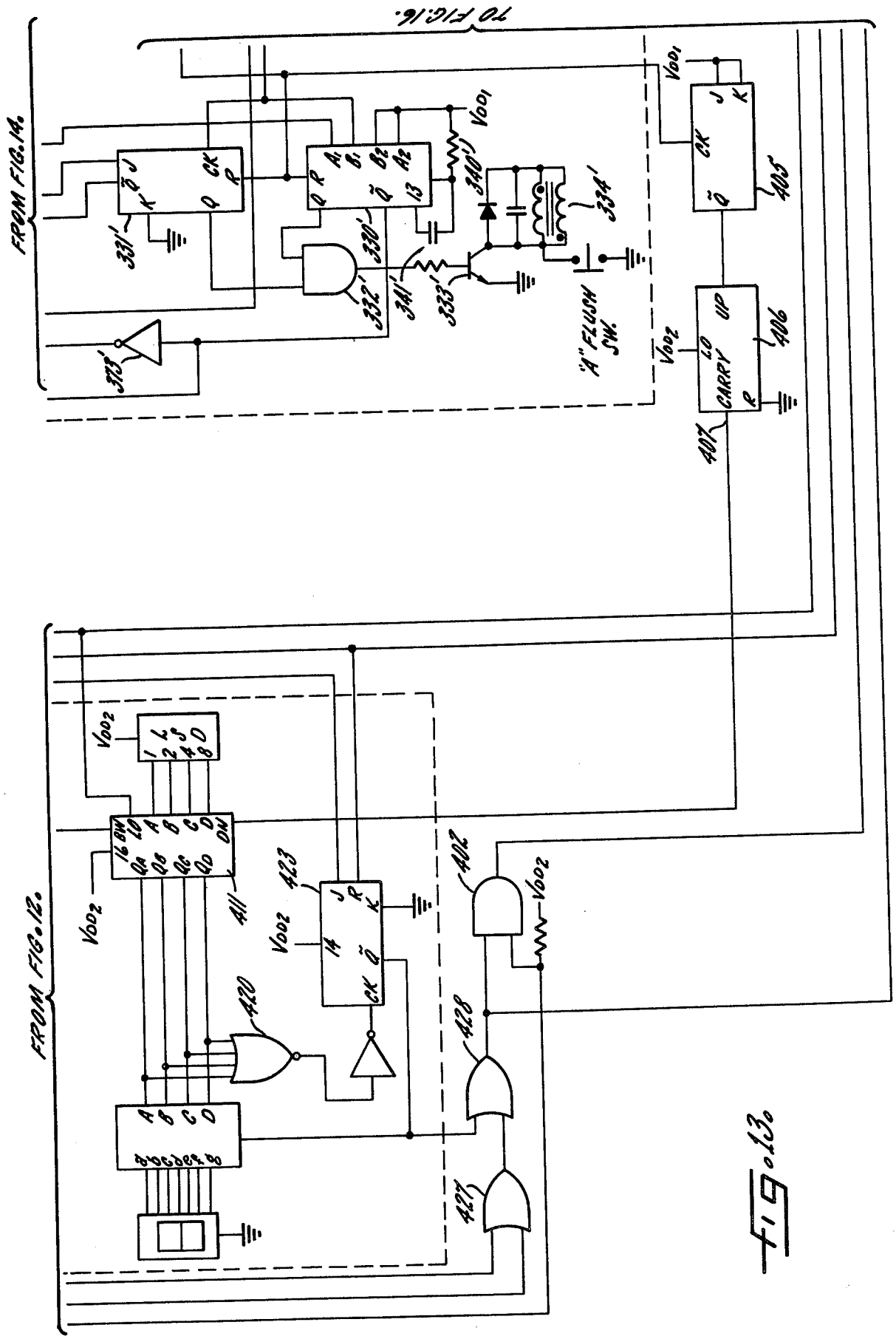

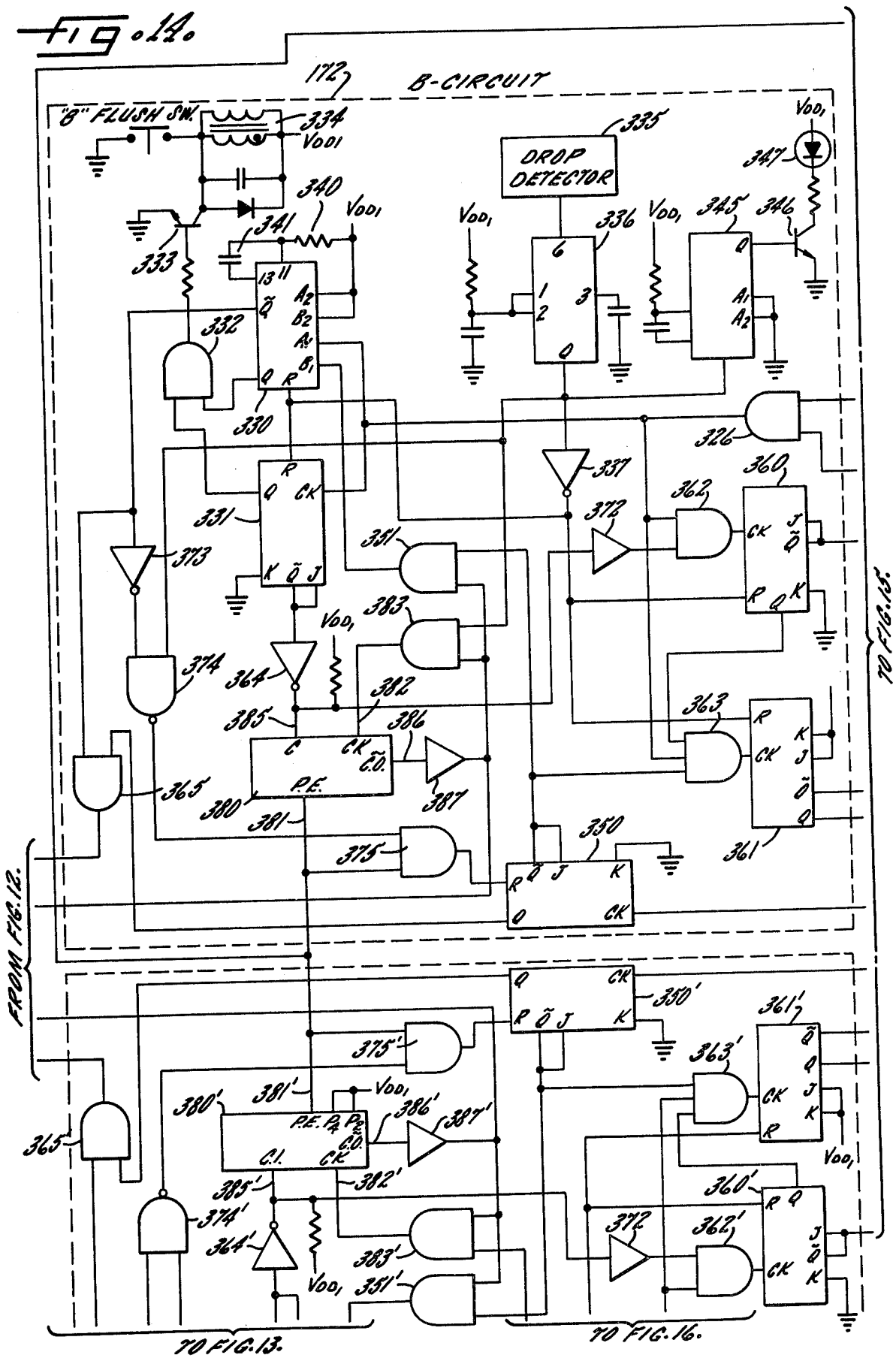

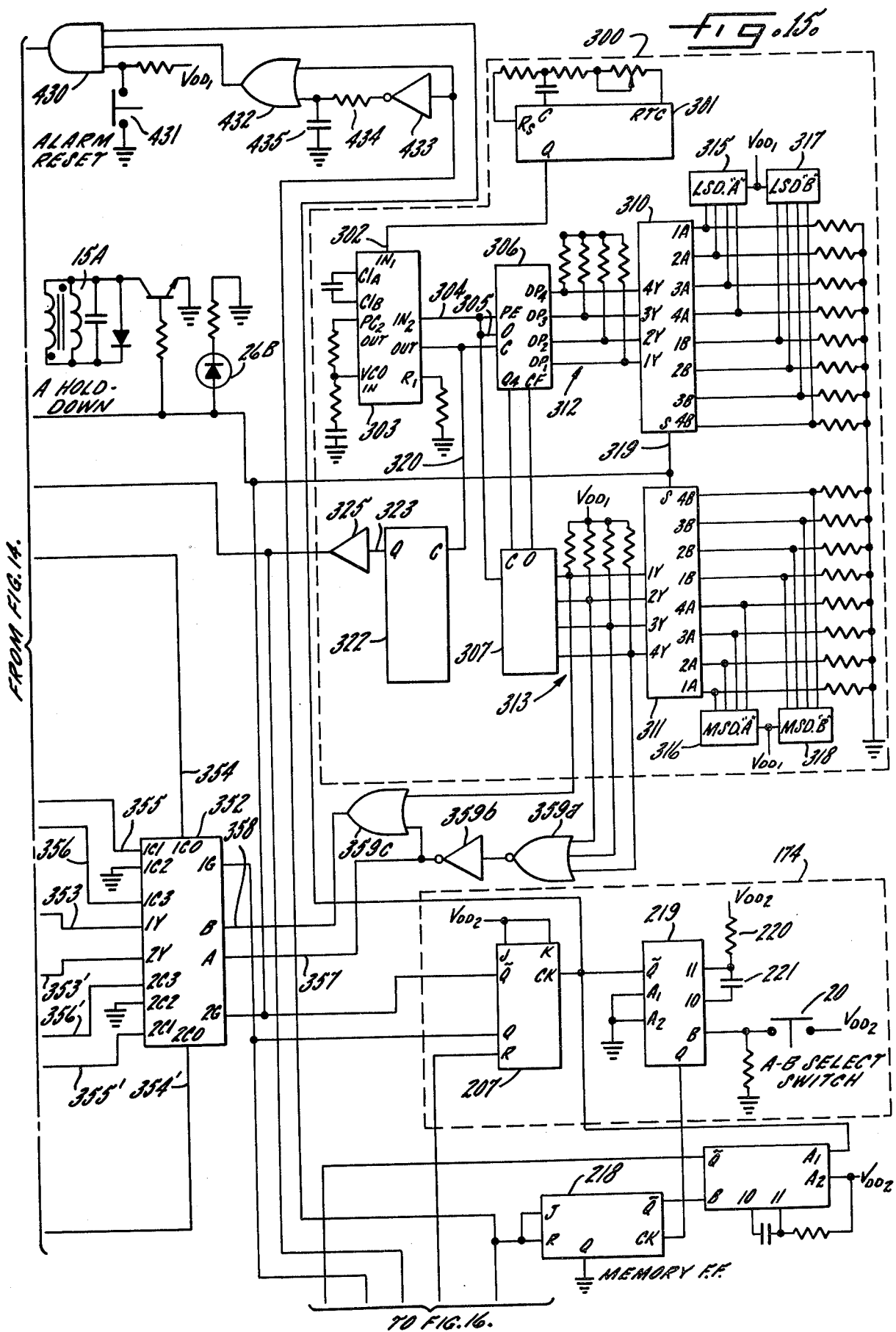

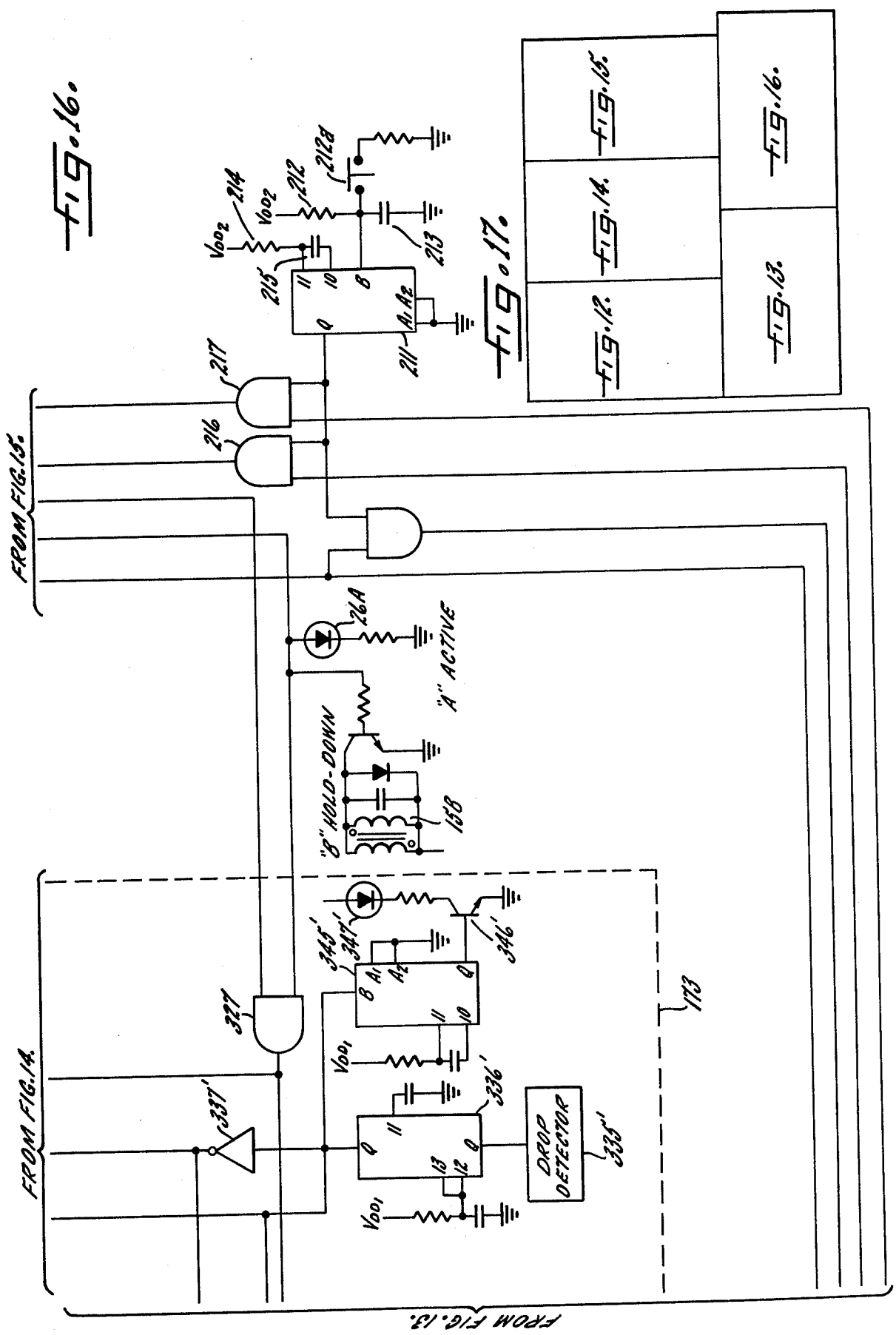

ELECTRONIC CONTROL MEANS FOR A PLURALITY OF INTRAVENOUS INFUSION SETS

BACKGROUND OF THE INVENTION

This invention relates generally to apparatus to controlling the flow of fluids, and in particular relates to electronic control apparatus for controlling the administration of a plurality of separate fluids independently and consecutively. The basic IV set itself may be of the type described in co-pending application Ser. No. 637,208, filed Dec. 3, 1975, or that shown in co-pending application Ser. No. 637,206, filed Dec. 3, 1975, both assigned to the same assignee as the present invention.

Still more specifically, the present invention relates to electronically controlled intravenous administration sets, wherein electrical circuitry is connected with a plurality of valve operators to operate a plurality of valves in a plurality of intravenous administration sets to control the flow of intravenous fluids from a plurality of separate sources.

Many different types of electronically controlled administration sets are known in the prior art. However, all such sets known to applicant are capable of electronically controlling only one intravenous fluid at a time, and do not have the means or capability of controlling a plurality of fluids by means of a plurality of valves.

Several factors are important in the intravenous administration of fluids, and include, among others, the necessity or desirability of preventing the injection of fluid into the tissue surrounding a vein in the event the needle is improperly inserted or becomes displaced from a vein into which the fluid is to be injected; the desirability of keeping the injection site open, or in other words, of preventing clotting at the injection site in the event the flow through the intravenous set is interrupted or ceases for some reason; the desirability of alarm means to indicate when the unit is not performing properly, as, for example, when the actual flow rate differs from the desired or preset rate; the desirability of the unit to operate even in the event of loss of power from the alternating current supply; the desirability of an accurate and easily read display of the volume and rate of fluid being administered; the necessity of obtaining an accurate and reliable rate of flow through the set; and the ability to control the flow of two separate fluids independently and consecutively, with circuit means connected with a plurality of valves to control the two fluids, and including circuitry to effect automatic switching from one set to the other, as, for example, when one side of the circuit goes into the alarm mode.

Moreover, a very serious problem in hospitals and the like is the occurrence of so-called "runaway" IV sets. This situation arises, for example, when an IV set is set by a nurse or other attendant for the administration of an IV fluid to a patient at a predetermined rate of flow, and subsequently the rate of flow increases for one reason or another. A further problem results from inaccurately setting conventional clamps and the like. The occurrence of flow rate of an intravenous fluid in excess of that desired or set is particularly critical in postoperative procedures, or in any other situation in which the patient has received anesthesia. This is due to the fact that various organs, such as the kidneys of anesthetized persons do not function properly for a brief time after having been anesthetized, and the body does not have the ability to rid itself of fluids at a desired rate. Accordingly, the fluid will build to a point where it can no longer be accommodated by the body's normal functions, and the fluid then begins to build in the person's lungs. This, of course, may result in pneumonia or other serious problems, and in fact, if left unattended, can be fatal.

With the present invention, the problems associated with prior art devices are overcome. More particularly, with the present invention injection of the intravenous fluid into the tissue at an injection site is avoided by making the intravenous administration set of the gravity feed type. The injection site is kept open in the present invention by the provison of the dual control feature, which enables the independent and consecutive control of a plurality of fluids, whereby in the event the primary fluid is exhausted or terminated for one reason or another, the secondary fluid is automatically caused to flow to keep the injection site open. For example, the primary fluid may be a medication or nutriment required after a surgical procedure or the like, and if the source of such fluid is depleted or flow thereof otherwise interrupted for some reason, the circuit automatically switches to the secondary fluid, which may be a saline solution, for example, which may be set at a flow rate considerably less than that of the primary fluid, as, for example, a rate sufficient only to keep the injection site open and prevent clotting thereat.

Also, the circuitry of the present invention includes sensing means for detecting the occurrence of a flow rate other than that set by the attendant and for sounding or giving an appropriate alarm, and also for arresting flow through the malfunctioning side of the apparatus until the situation is corrected. This, of course, prevents either the failure to inject a desired fluid or the injection of an undesired amount of a desired fluid.

Further, the present invention includes both an ac and dc powered capability, whereby the set can continue to operate even in the event of loss of ac power thereto, as, for example, during transport from one location to another or in the event of a power failure or inadvertent unplugging of the set from an ac outlet and the like.

Additionally, the present invention includes an easily read LED display for accurately and reliably indicating the amount of fluid to be dispensed in a metered cycle.

Moreover, the electronic control of the present invention includes a memory capability, whereby it remembers the amount of fluid remaining to be dispensed, in the event a dispensing cycle is interrupted.

Still further, one form of the invention includes a digitally settable clock, and further includes circuitry for time sharing of the clock by the two supply circuits for the respective fluids to be controlled.

OBJECTS OF THE INVENTION

It is an object of this invention to provide electronic control apparatus for controlling the administration of a plurality of separate fluids independently and consecutively.

Another object of the invention is to provide an electronically controlled intravenous administration set, wherein the set includes electrical circuitry for controlling the operation of a plurality of valves in a plurality of sets, whereby the flow of a plurality of separate intravenous fluids may be controlled with the apparatus.

A still further object of the invention is to provide a dual flow electronically controlled intravenous administration set, which includes means for controlling the flow through a plurality of sets and has circuitry associated with the control of each set, with means for automatically switching from one set to the other under predetermined circumstances.

An even further object of the invention is to provide an electronically controlled intravenous administration set wherein electrical circuitry is provided for controlling the flow of a plurality of separate intravenous fluids, and includes means for producing an alarm in the event of flow either less than or greater than the desired rate by a predetermined amount.

Another object of the invention is to provide an electronically controlled intravenous administration set which includes means for automatically keeping the injection site open in the event the flow of intravenous fluid from the primary source is interrupted or terminated.

A further object is to provide an electronic control for administering intravenous fluids, which includes a digitally settable clock, time shared by a plurality of circuits for controlling flow of a plurality of fluids.

Yet another object is to provide an electronically controlled means for independently and consecutively controlling the dispensing of a plurality of fluids, said means including electrical circuitry having memory capability for remembering the amount of fluid remaining to be dispensed, in the event a dispensing cycle is interrupted.

BRIEF DESCRIPTION OF THE DRAWINGS

FIGS. 6, 7, 8, 9 and 10 are schematic diagrams of portions of the electrical circuit in a first form of the invention, wherein FIG. 6 shows the supply and B circuit for controlling flow at one side of the device, and the A-B select circuit; FIG. 7 shows the circuit for controlling the B side of the apparatus and also shows the divide by 15 counter; FIGS. 8 and 9 show the volume slector and monitor portions of the circuit for the electronically controlled device; and FIG. 10 shows the A-B select circuit and memory. FIG. 11 is a view illustrating the manner in which FIGS. 6, 7, 8, 9 and 10 are relatively placed to be read.

FIGS. 12–16 are schematic circuit diagrams of a second form of control for the invention, wherein:

FIG. 12 shows the alarm circuit and a portion of the volume selector and monitor circuit;

FIG. 13 shows a portion of the volume selector and monitor circuit, and a portion of the A-circuit;

FIG. 14 shows the B supply circuit and a portion of the A-circuit;

FIG. 15 shows the digitally settable click, A-B select circuit and memory; and

FIG. 16 shows a portion of the A-circuit and means for clearing the volume counter.

FIG. 17 is a view illustrating the manner in which FIGS. 12, 13, 14, 15 and 16 are relatively placed to be read.

DETAILED DESCRIPTION OF THE PREFERRED EMBODIMENTS

Figure 1:
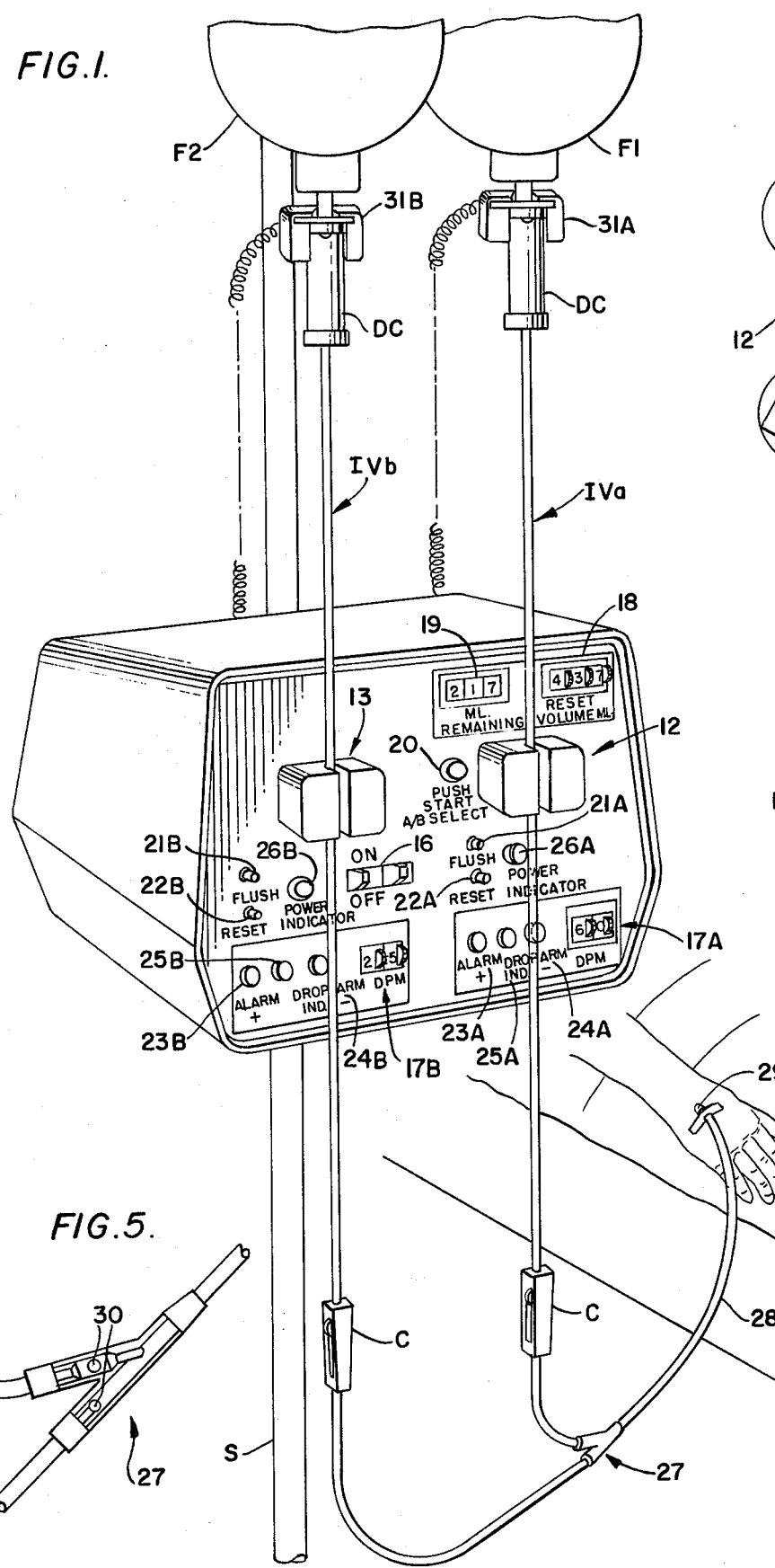
FIG. 1 is a perspective view of an electronically controlled apparatus according to the invention, shown as used to control flow from a pair of independent sources of intravenous fluid.

In the drawings, wherein like reference numerals indicate like parts throughout the several views, an electronically controlled apparatus 10 for controlling the flow of a plurality of separate intravenous fluids F1 and F2 comprises a console of housing 11 supported on a suitable support stand or the like S, which may also support the fluids F1 and F2.

Figure 3:
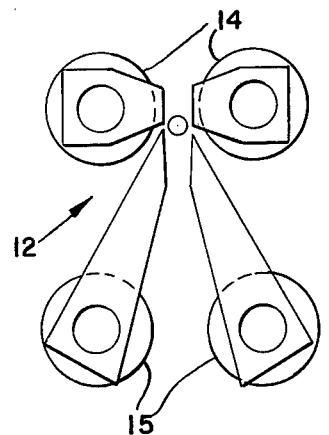
FIG. 3 is a schematic view of a pair of electromagnets used to control a valve in accordance with the invention.
Figure 4:
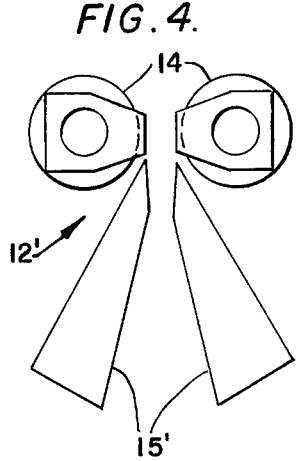
FIG. 4 is a view similar to FIG. 3 of a modified arrangement for controlling the valve, wherein electromagnets are used to open the valve and permanent magnets are used to hold the valve closed.

The console unit 11 has built thereinto a pair of valve control means or assemblies 12 and 13, each comprising an electromagnet 14 positioned to open a valve associated with a respective intravenous set IVa and IVb, and a magnet means 15 to hold the valve closed to prevent backflow through the set, as for example, in the event the outlet therefrom is elevated higher than the valve. As seen in FIG. 3, the magnet means 15 may comprise electromagnets, or as seen in FIG. 4, the magnet means 15' may comprise permanent magnets to hold the valve closed when the electromagnet 14 is not energized.

An on-off switch 16 controls supply of power to the apparatus, and the valve control means or assemblies 12 and 13 are connected in electrical circuitry which controls energization of the valve operating means to control the rate of opening and closing of the valve means in the associated IV set, to thus control the rate of flow of the respective fluids F1 and F2. These rates are accurately established by means of suitable manually operated control knobs or the like 17A and 17B for the primary fluid F1 and the secondary, or keep-open fluid F2, respectively. Numerals are associated with the control knobs or the like 17A and 17B for visually indicating the selected drop rate. Thumbwheels 18 are provided for presetting a desired volume to be administered in milliliters, for example, and numerals are associated therewith for giving a visual indication of the volume selected. A digital display 19 indicates the volume remaining to be administered at any given time.

When the on-off switch 16 is turned to "On" to supply power to the apparatus, side B of the circuit is automatically energized, and flow starts on side B at the preset rate. An A/B select or push-start button 20 is provided for disabling side B and enabling or energizing side A to obtain a preset rate and volume of flow through the intranvenous set IVa. Thereafter, each time the A/B select button is depressed control is switched from the operational to the alternate supply. During normal running of side A, there is a continuous readout of volume to be administered. In the event of a disparity, an alarm is given, and the display remains on. If no alarm condition occurs, the unit will continue to run at the preset rate until the volume to be administered reaches zero. The circuit then automatically switches to side B, and runs at the rate set on that side until the fluid F2 is depleted or some problem causes the unit to go into alarm.

In the event that side A is to be run independently, no IV set is connected to side B. Side A will thus run at the preset rate until the present volume is administered and will then shut down and give the appropriate alarm signal.

Flush buttons 21A and 21B are associated with both sides of the apparatus for overriding the control circuit to flush the set, and reset buttons 22A, 22B are provided to reset the circuits. High and low rate indicating lights or the like 23A, 24A and 23B, 24B are provided on the respective sides A and B for indicating abnormal conditions, and lights 25A, 25B are associated with sides A and B, respectively, for visually indicating when a drop falls. This enables an attendant to manually check the drop rate, for example. Power indicator lights 26A and 26B are also associated with the respective sides to indicate when that side is energized or running.

The intravenous administration sets IV$a$ and IV$b$ each includes a drip chamber DC of conventional design connected with the respective fluids F1 and F2, and constructed in a known manner to obtain a desired drop size, as for example, such that 15 drops equal 1 milliliter. A clamp C may be provided on the length of tubing, if desired, for shutoff of flow through the respective sets. Additionally, the lengths of tubing associated with the intravenous administration sets IV$a$ and IV$b$ are each connected with a Y-connector 27, which has a further length of tubing 28 connected therewith and extending to a cannula or the like 29, which is inserted into a patient.

Figure 5:
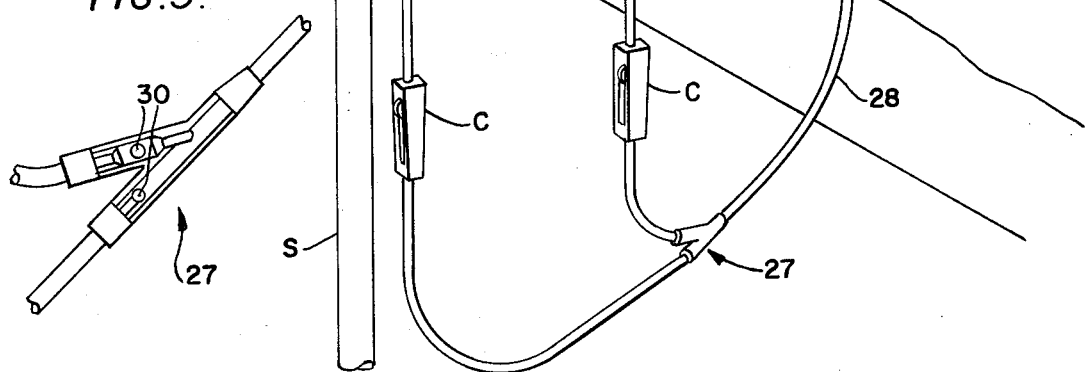
FIG. 5 is a fragmentary, perspective view, with portions broken away, of the Y-connector used to join the lengths of tubing connected with the two sources of intravenous fluid in FIG. 1 with the length of tubing joined to the cannula and thus to the patient.

As seen in FIG. 5, the Y-connector 26 may have a pair of check valves 30 therein for preventing backflow through the branches of the Y-connector into the respective intravenous administration sets.

Rather than use a Y-connector such as 27, the set may utilize a pair of "piggy back" needles or the like, if desired.

Suitable drop detector assemblies 31A and 31B are associated with the respective drip chambers DC for detecting the presence of a drop falling through the drip chambers and producing a signal in response thereto, which is supplied to the unit 11 for effecting control of the valve control means.

The circuitry includes a divide by N counter, which converts drops to milliliters, which in turn are displayed, the drop size being predetermined such that a predetermined number of drops equals a predetermined volume. As noted previously, during normal operation, there is a continuous readout of the volume of fluid to be administered. When the down counter in association with the A circuit reaches zero, an A/B select circuit automatically switches control back to side B, which then runs at a rate equal to the setting on control knob or the like 17B until the fluid F2 is exhausted, or until some other problem causes the alarm to sound.

The circuitry includes means for automatically energizing electromagnets 15 when the electromagnets 14 are de-energized, and thus backflow is prevented in the event one container should be positioned higher than the other, or some other condition should occur which would tend to promote backflow.

Figure 2:
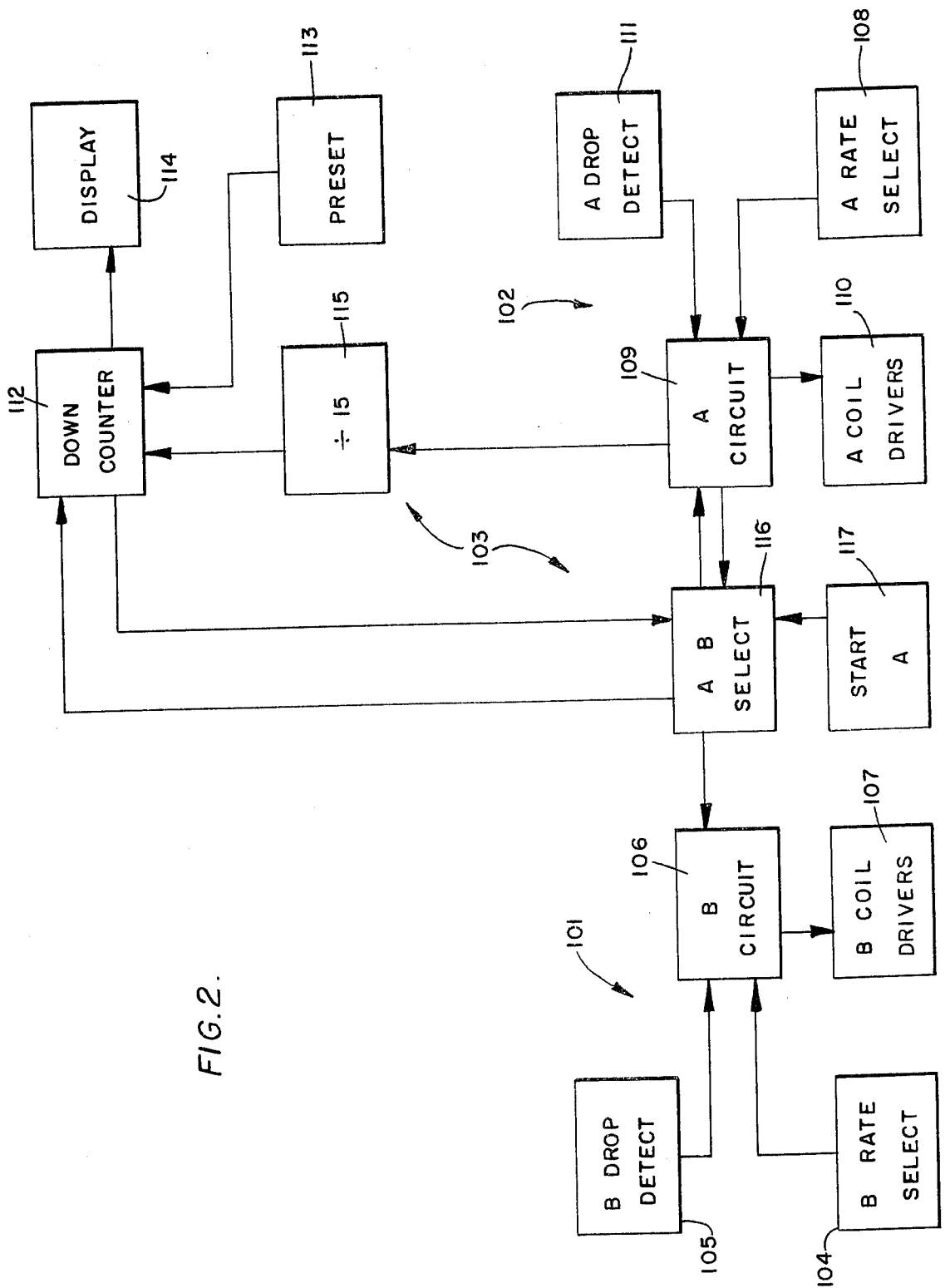
FIG. 2 is a block diagram of the basic elements of the apparatus according to the invention.

A block diagram illustrating the general structure and function of a dual IV set control constructed in accordance with the present invention is shown in FIG. 2, and for ease of understanding, the following description will treat the electronic IV set controls as two separate and distinct units constrained to function as determined by the master control to be described therein. However, it will be apparent to one skilled in the art that certain manufacturing economies may be achieved by providing certain common circuit elements to be shared by the two electronic IV controls, as described herein with reference to the embodiment in FIGS. 12–16, for example.

The control circuit includes first and second electronic IV controls 101, 102 and master control 103 for determining which of the IV controls will control supply of fluid to a patient. The IV control 101 may be considered the B fluid supply described above, and is adapted to simply supply fluid at a preselected drop rate. The IV control 102 is coupled to the master control 103 to function as the A supply described above, for allowing an attendant to preselect a volume of fluid to be dispensed, for dispensing such volume at a preselected rate and for terminating the supply when the preselected volume is dispensed. The master control 103 controls switching between the circuits 101 and 102 and further functions with the A circuit in metering the volume of fluid delivered.

As more fully described hereinafter, and also as described in the above referenced patent applications, the electronic IV control generally indicated at 101 includes a drop rate selector 104 for opening the IV set valve at a preselected rate to allow drops to form and fall at that rate and a drop detector 105 for sensing each drop falling through the drip chamber and closing the valve in response thereto. More specifically, the rate selector 104 controls the frequency of a variable frequency clock to produce one pulse for each desired drop, the B control circuit 106 responding to each clock pulse by energizing coil driver 107 to energize electromagnet 14 to open the IV valve. Opening of the valve allows a drop to form and fall in the drip chamber. The falling drop is sensed by the drop detector 105 which sends a signal to the control circuit 106 to cause the closing of the valve. The IV control 101 includes a no drop detector operative in response to the failure of a drop to form and fall to prevent further energization of the coil drivers 107, thereby to stop the flow of fluid, and to energize audible and/or visual alarms (not shown) for informing an attendant of a malfunction.

The A circuit 102 contains similar elements including an A rate selector 108 operating in conjunction with an A control circuit 109 for opening the valve in the A circuit via the A coil drivers 110. As with the B circuit, the A circuit includes a drop detector 111 adapted to sense each drop falling through the drip chamber and cause the closing of the valve by deenergizing the coil drivers 110.

According to one feature of the invention, means are provided, operational in conjunction with the A circuit, for metering the total volume of fluid F1 to be dispensed in a cycle. To that end, the A circuit 102 is coupled to the master control circuit 103, which responds to signals indicative of the falling of a drop, and is adapted to count such signals to measure the amount of fluid actually dispensed. The master control circuit 103 includes metering counter 112, presettable via the operator accessible digital switches 113 (18 in FIG. 1). In practice, an attendant presets the volume of desired fluid via the switches 113, thereby setting the modulus for the counter 112. The associated display 114 (19 in FIG. 1) responds to the number within the counter for indicating the amount of fluid yet to be dispensed. It is preferred that counter 112 be constructed as a down counter so that the display 114 indicates the volume of fluid remaining to be dispensed. In an alternative configuration, the counter 112 may be constructed as an up counter, arranged to count from zero to the number preset on the switches 113, the display 114 in such configuration indicating the volume of fluid actually dispensed.

For relating the number of drops to the volume of fluid dispensed, a divide by N counter, shown herein as divide by 15 counter 115 is coupled to the A control circuit 109 and responds to signals produced by the drop detector 111. The divide by 15 counter 115 is adapted to clock the metering counter 112 once for each 15 drops dispensed by the A circuit. As noted above, the drip chamber is of conventional construction and is arranged and constructed to control the size of drops so that a predetermined number of drops make up a known volume of fluid. In the illustrated embodiment, the drip chamber used is of the type wherein 15 drops comprise one milliliter of dispensed fluid. To use the illustrated circuit with drip chambers of other constructions, such as those dispensing 20 or 60 drops per milliliter, it is necessary only to modify the construction of the divide by N counter 115 to divide by the proper number of drops.

It will now be apparent that the counter 112 may be preset to dispense any number of milliliters of fluid, the A circuit may be energized to initiate the dispensing, and the counter 112 and divide circuit 115 monitor the fluid dispensed to continually indicate via the display 114 the amount of fluid yet to be dispensed.

In accordance with the invention, the master control 103 includes means for selectively energizing the IV controls 101, 102 to allow dispensing of different fluids at individually preselected rates. To that end, the master control 103 includes an A/B select circuit 116 coupled to the B control circuit 106 and the A control circuit 109 and functioning to energize one or the other of such circuits to allow the dispensing of fluid thereby. The A/B select circuitry 116 includes means for energizing the B circuit 101 when power is first applied to the unit. Accordingly, the B circuit will control the dispensing of fluid unless, of course, an alarm condition is detected at which point the system will enter the alarm mode and fluid dispensing will be terminated. An attendant may initiate the dispensing of a predetermined volume of fluid via the A circuit, by actuating the switch 20 on the control panel which energizes a start A circuit 117 to cause the A/B select circuitry 116 to change states, deenergizing the B circuit 101 and energizing the A circuit 102. In addition to switching control to the A circuit, the A/B select circuit 116 acts upon the counter 112 to strobe the number preset on the switches 113 into the counter. The A circuit then functions to dispense the fluid at the rate seleced by rate selector 108, dispensing of each 115 drops causing the clocking of the down counter 112. When the counter 112 is cycled to zero, indicating the dispensing of the preselected amount of fluid, the counter produces a signal which acts upon the A/B select circuit 116 to switch control from the A circuit back to the B circuit. An attendant observing the unit functioning on the B supply and indicating zero milliliters remaining to be dispensed on the A supply will realize that the A circuit has operated successfully through its entire cycle and at the termination thereof switched control back to the B circuit.

As with the B circuit, the A circuit also includes an alarm system for indicating malfunction. In the event an alarm condition develops while the A circuit is functioning to dispense its predetermined volume, the A circuit 109 will sense such alarm and in response thereto prevent the further energization of coil drivers 110, thereby terminating the supply of fluid from the A source, F1, upon this occurrence, the A circuit, being coupled to the A/B select circuit 116, causes the select circuit to change states, automatically activating the B supply 101 for dispensing B fluid F2 at the preselected rate established therefor. The A/B select circuit 116 functions to lock the counter 112 into the state existing at the time of the alarm so that the display 114 indicates to an attendant the amount of fluid remaining to be dispensed at the time the system went into the alarm mode. The B supply functions to keep the injection site open until the attendant is appraised of the alarm condition and clears it. When the alarm condition is cleared, the attendant then returns control to the A supply via depression of the appropriate pushbutton switch 20. As opposed to initiation of a cycle wherein such initiation serves to load the counter 112 to the number preset on the switches 113, the A/B select circuit 116 functions when returning to an interrupted cycle to prevent the reloading of the counter 112 so that the counter retains the previous number and begins to count down from that number to zero. Thus, the counting circuitry remembers the amount of fluid still to be dispensed in an interrupted cycle and dispenses only that amount of fluid when control is returned.

Embodiment I

Figure 6:
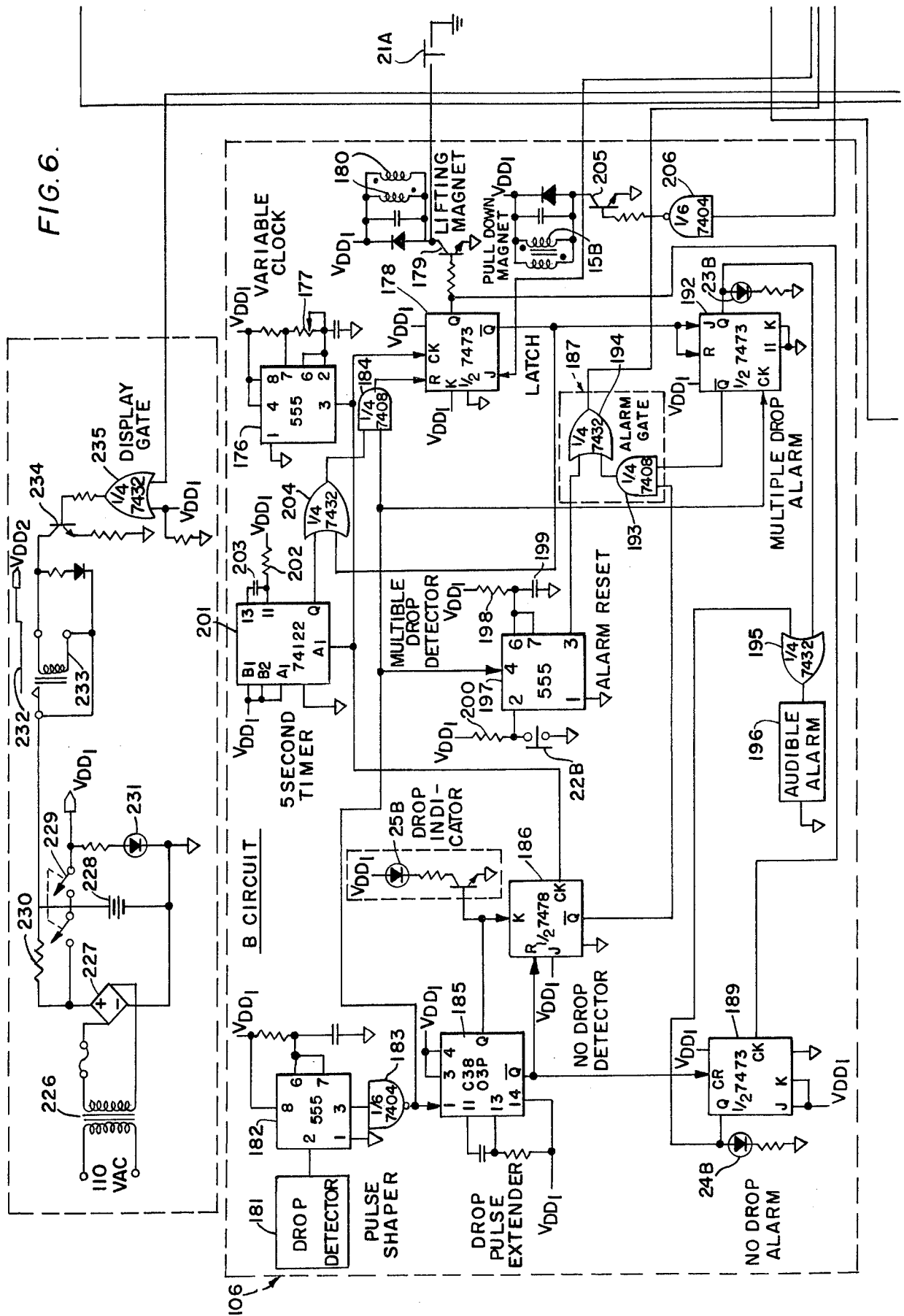
Figure 7:
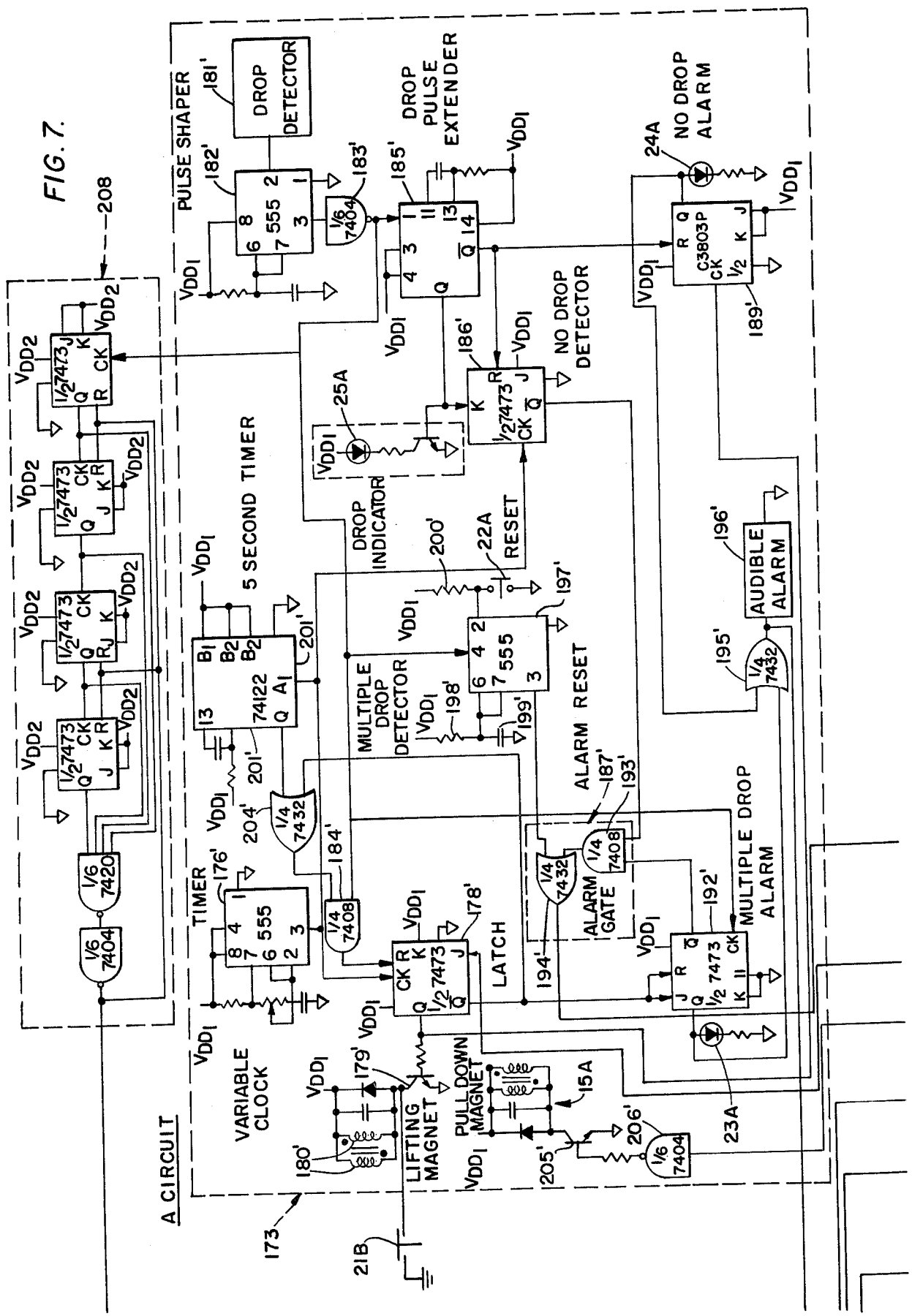

Turning now to FIGS. 6–11, there is shown the circuitry of a first embodiment of the dual IV control illustrating the present invention. Referring first to FIG. 6, there is shown the B circuit control 106, much as described in co-pending application Ser. No. 637,206, referenced above. The circuit includes a transistor switch 179 for controlling the operation of the IV valve 14 (see FIG. 3) in the B supply circuit via the valve coil 180. The switch 170 is driven from a latch, shown herein as flip-flop 178, the Q output of which is coupled to the base circuit of switch 179 so that the flip-flop in its set condition energizes the switch to energize the coil to thus open the valve.

For opening the valve at an operator preselected rate, a variable clock 176 is provided having an output coupled to the clock input of the latching flip-flop 178. A potentiometer 177 in the timing circuit of the clock 176 allows an attendant to select the clock frequency and thereby establish a desired drip rate. The latching flip-flop 178 has its K input tied to the positive supply of voltage and its J input supplied from a B latching gate 188, to be described below. In normal operation, the J input is at a high level at the time the variable clock 176 produces a valve opening clock pulse. As a result, the latching flip-flop 178 will respond by changing states, driving its Q output high and energizing the switch 179.

A drop detector 181, operatively associated with the drip chamber, may be configured as described in the above referenced patent application. Briefly, the drop detector includes a light source optically coupled to a photosensor so that any drop of fluid falling through the drip chamber will interfere with the light falling on the photosensor to produce an output signal. This output serves as a clock input for pulse shaper 182, in the form of a conventional monostable multivibrator, resulting in the production of a pulse at the output of the pulse shaper 182 for each drop sensed by the drop detector 181. It is seen that the pulse from the pulse shaper 182 is coupled to the reset input of the latching flip-flop 178 via inverter 183 and AND gate 184, thereby resetting the latching flip-flop 178, driving its Q output low, deenergizing the transistor switch 179 and thus deenergizing the coil 180 and allowing the valve 14 in the B supply to close.

A further monostable multivibrator or drop pulse extender 185 is driven by the pulse shaper 182 via inverter 183 so as to produce a pulse of sufficient duration in response to each drop falling through the drip chamber to allow the visible flashing of a drop indicator light 25B. An operator observing the periodic flashing of the drop indicator 25B at the rate selected by the variable clock 176 is appraised that the system is operating properly.

For sensing errors in the flow rate and preventing further energization of the valve in response thereto, an alarm system is provided, such alarm system including both low and high rate alarms. The low rate or no drop alarm includes a second flip-flop 186 having its clock input driven from the variable clock 176 and its reset input driven from the drop pulse extender 185. The K input of the flip-flop 186 is coupled to the Q output of 185.

In normal operation, therefore, the appearance of a clock pulse at the clock input of the flip-flop 186 will occur with the J input high and K low so that the flip-flop will be clocked to drive its $\bar{Q}$ output low. Upon detection of a drop, the drop pulse extender 185 will couple a signal to the reset input of the flip-flop, resetting it to the opposite condition with the $\bar{Q}$ output high. It will be appreciated that in normal operation the latching flip-flop 178 and flip-flop 186 change state generally in synchronism, being driven to a first state in response to a clock pulse and a second state in response to a drop pulse. However, when no drop is detected, neither the latching flip-flop 178 nor the flip-flop 186 is reset as described above. The $\bar{Q}$ output of the flip-flop 186 is, therefore, maintained in its low condition, this low signal being passed through alarm gate 187 and the B latching gate 188 in the master control circuit to appear as a low signal on the J input of the latching flip-flop 178. As a result, when the next clock pulse is generated by the timer 176, the flip-flop 178 will respond thereto by driving its Q output low, thereby deenergizing the switch 179 and coil 180 and allowing the valve 14 in the B supply to close. Because the J input of the flip-flop 186 is tied to positive voltage and the K input is maintained low by the drop pulse extender 185, the flip-flop 186 will respond to successive clock pulses by maintaining its $\bar{Q}$ output low, thus maintaining the J input of the latching flip-flop 178 at a low level. As a result, the latching flip-flop 178 will be maintained in condition with its Q output low, preventing further energization of the switch 179 and further energization of the valve coil 14, with the result that opening of the valve is prevented.

For indicating a low rate alarm condition to an attendant, a no drop alarm is provided, shown herein as flip-flop 189 and low rate or no drop indicator light 24B. The flip-flop 189 has a reset input driven from the $\bar{Q}$ output of the drop pulse extender 185. The J and K inputs of the flip-flop 189 are tied to the positive supply of voltage so that the flip-flop will attempt to toggle for each clock pulse received. It is seen that the clock input of the flip-flop 189 is driven from the Q output of the latching flip-flop 178. As a result, the flip-flop will attempt to toggle each time the Q output of the latching flip-flop 178 is driven to a low level to deenergize the switch 179. However, in normal operation, this clocking will occur while the $\bar{Q}$ output of the drop pulse extender is maintaining a low level on the reset input of the flip-flop 189. The reset input will control and accordingly the Q output of the flip-flop 189 will be maintained at a low level. However, in the absence of a detected drop, and when the latching flip-flop 178 is returned to its Q low condition by the second clock pulse without an intervening drop pulse, the clock signal will be coupled to the flip-flop 189 without an overriding reset signal from the drop pulse extender 185. As a result, the flip-flop 189 will be caused to change states, driving its Q output high and illuminating the no drop indicator 24B. Because the latching flip-flop 178 is prevented from changing state during this alarm condition, no subsequent clock pulses will be provided to the no drop alarm 189 and it will be maintained in its alarm condition.

In addition to the no drop or low rate alarm 189, the B supply circuit illustrated in FIG. 6 includes means for detecting high rate alarm conditions, or multiple drops, and, in response thereto, putting the supply circuit into an alarm condition. The multiple drop detector includes a multiple drop alarm flip-flop 192 having the clock input thereof driven by the output of the pulse shaper 182. It is seen that the K input of the flip-flop 192 is connected to ground while the reset and J inputs are driven from the $\bar{Q}$ output of latching flip-flop 178. A high rate alarm indicator 23B is driven by the Q output of multiple drop alarm flip-flop 192 and, as will become more apparent, is illuminated when drops are detected out of the normal operational cycle.

Remembering that the $\bar{Q}$ output of the latching flip-flop 178 is driven low when the flip-flop is triggered to open the valve, it is seen that this condition maintains the multiple drop alarm flip-flop 192 in its reset condition. Detection of a drop causes the pulse shaper 182 to produce a pulse which is coupled via inverter 183 and AND gate 184 to the reset input of latching flip-flop 178. The pulse passed by inverter 183 is also coupled to the clock input of flip-flop 192, and attempts to clock that flip-flop to its set condition. However, the latching flip-flop 178 has not yet reverted to its reset condition and, thus, the reset input maintained by the $\bar{Q}$ output of flip-flop 178 overrides the clock signal on the flip-flop 192 and maintains the multiple drop alarm flip-flop in its reset condition. However, after the latching flip-flop 178 switches to its valve closed position, the reset signal is removed from flip-flop 192 and it is then adapted to respond to further clock pulses. If a drop is then sensed, the pulse shaper 182 will cause the production of a further clock pulse, such pulse being coupled to the clock input of multiple drop alarm flip-flop 192, causing that flip-flop to change states to drive its Q output high. As a result thereof, the multiple drop indicator 23B will be illuminated. In addition, the $\bar{Q}$ output of flip-flop 192 having gone to its low condition, passes that low signal through AND gate 193 and OR gate 194 in the alarm gate 187 and through the B latching gate 188 to impose a low signal on the J input of the latching flip-flop 178. This, it is recalled, is the condition which inhibits flip-flop 178 from responding to clock pulses to drive the Q output high, thereby maintaining the associated valve in the closed position. It is further seen that the Q outputs of the multiple drop alarm flip-flop 192 and no drop alarm flip-flop 189 are coupled to the inputs of an OR gate 195 so that when either of the alarms is actuated, the output of the OR gate will cause the energization of an audible alarm 196.

For resetting the visual and audible alarms and returning the supply circuit to its non-alarm condition, an alarm reset circuit is provided. In the illustrated embodiment the alarm reset circuit includes a monostable multivabrator 197 having a period established by resistor 198 and capacitor 199, such period being longer than the period associated with the slowest clock frequency of interest. The trigger input of the multivibrator 197 is coupled via resistor 200 to the positive voltage supply and through a normally open, user accessible reset switch 22B to ground. Depression of the reset switch 22B triggers the monostable 197 to drive the output thereof high for the time period associated therewith. That output is coupled through OR gate 194 in the alarm gate 187 to the B latching gate 188. Recalling that the output of OR gate 194 is maintained low in an alarm condition, it is seen that the alarm reset multivibrator 197, when triggered, overrides that low signal and causes the output of OR gate 194 to be switched high for the period of the monostable. That high signal is passed through B latching gate 188 to the J input of latching flip-flop 178, allowing that flip-flop to respond to the next clock pulse received to drive the Q output high, energizing the switch 179, and opening the IV valve. If the alarm condition has been caused by a high drop rate condition, switching of the flip-flop 178 to its $\overline{Q}$ low condition will serve to clear the alarm by imposing a reset signal on multiple drop alarm flip-flop 192. Contrariwise, if the alarm has been initiated by a low drop rate condition, detection of a drop following the change of state of flip-flop 178 will trigger the drop pulse extender 185, driving its $\overline{Q}$ output low and imposing a reset signal on the no drop alarm flip-flop 189. Thus, depression of reset switch 22B initiates a period for overriding the low signal on the J input of the latching flip-flop for a time sufficient for that flip-flop to respond to the next clock pulse. Proper response to the next clock pulses serves to complete the clearing or resetting of the supply circuit.

For preventing the valve in the IV set from remaining open for an excessive period of time, maximum time limit means are provided, shown herein as five second timer 201 and its associated components. The timer 201 is of the retriggerable variety and has a clock input driven from the output of the variable clock 176. Resistor 202 and capacitor 203 establish the period for the timer 201 which is selected as the maximum desired valve open time, such as five seconds. Each clock pulse produced by the variable clock 176 serves to reinitiate the period of the timer 201. If the maximum time elapses before a drop is detected, the timer 201 will time out, driving the output thereof low. That low signal is coupled through OR gate 204 and AND gate 184 to the reset input of the flip-flop 178, resetting that flip-flop. Thus, even if no drop is detected, the timer 201 will serve to positively close the valve after the maximum desired open period.

As a further feature of the illustrated circuit, means are provided for maintaining the IV valve of the non-operating supply circuit in the positively closed position, such means being implemented herein by way of pull down magnets indicated generally in FIG. 3 as 15. In the circuit of FIG. 6, it is seen that the pull down magnets 15B are energized by providing base drive to switching transistor 205 via inverter 206, that inverter being driven by the $\overline{Q}$ output of the A/B select flip-flop 207 in the select circuit 174. Thus, when the A supply is operational, the low $\overline{Q}$ output of the select flip-flop will cause the output of inverter 206 to go high, providing base drive to transistor 205, and continually energizing pull down magnets 15B to maintain the valve in the B supply circuit on its seat.

A Supply Circuit

With two exceptions, the A supply circuit is identical to the B supply circuit, the common elements being indicated by primed numbers. Those elements will not be described further herein. With respect to the two variations, it is seen that the output of the pulse shaper 182', in addition to being connected as described previously, is also connected to the clock input of divide by 15 counter 208. The divide by 15 counter is adapted to relate drops of fluid delivered by the A circuit to volume of fluid delivered, the output of the divide by 15 counter being coupled to the volume selector and monitor circuit 175 for monitoring the volume of fluid delivered.

With regard to the second variation, the output of OR gate 195', in addition to being coupled to the audible alarm 196', is also connected via inverter 209 to B reset gate 210. As will be described in more detail below, the B reset gate 210 is adapted to switch control from the A circuit to the B circuit upon the occurrence of predetermined conditions. It will now be apparent that one of those predetermined conditions is an alarm condition when operating on the A supply circuit, occurrence of the alarm condition serving to switch control to the B circuit for keeping the needle open until the A circuit alarm is cleared.

To allow flushing of the IV sets, the switching transistors 179, 179' in the respective supplies are paralleled by flush switches 21A, 21B. If desired, the switches 21A, 21B may be ganged with their associated reset switches 22A, 22B so that flush and reset operations occur simultaneously.

In practicing the invention, means are provided for selectively energizing the A supply and B supply so that only one of such supplies is active at any given time, and for switching control between such supplies. To allow only one supply to be energized at any given time, and to selectively energize such supplies in dependence upon control signals, bistable means are provided for energizing the A supply in one stable state and the B supply in the alternate stable state. More specifically, A/B select flip-flop 207 is provided having its Q output coupled to the A latching gate 188' and its $\overline{Q}$ output coupled to the B latching gate 188. As a result, when the flip-flop 207 is in its set condition, the high Q output thereof applied to the input A latching gate 188' will allow the signal on the $\overline{Q}$ output of the no drop detector 186' to be passed through such gate to control the J input of the latch 178'. In normal operation, therefore, the latch 178' will be permitted to respond to each clock pulse to open the A supply valve, and in the alarm condition will be constrained to prevent further energization of the A valve. Further, in the set condition, the low $\overline{Q}$ output of flip-flop 207 will maintain the output of B latching gate 188 in a low condition, which, just as in the alarm condition, prevents energization of the switch 179 controlling the B supply valve. Contrariwise, when the flip-flop 207 is in its opposite or reset condition, the low Q output will act through A latching gate 188' to prevent energization of A supply switch 179', and the high $\overline{Q}$ output will allow the passage of signals from the no drop detector 186 through the B latching gate 188 to control the B supply latch 178. In addition, with the Q output of flip-flop 207 low to maintain the A supply deactuated, the low Q signal is applied through inverter 206' to provide base drive to transistor 205' thereby energizing the pull down magnets 15A to keep the A supply valve locked on its seat. The B latching gate 188 and B supply pull down magnet circuitry is driven from the $\overline{Q}$ output of the A/B select flip-flop 207 so that the condition of the B circuitry is exactly opposite that of the corresponding A circuitry (except, of course, if both supply circuits are in the alarm condition).

The flip-flop 207 is also used to drive the A side and B side power indicators, indicator 26A being driven from the Q output and indicator 26B from the $\overline{Q}$ output. To assure that the B circuit is energized when the system is first switched on, means are provided for resetting the flip-flop 207 upon the application of power. To that end, a power on monostable multivibrator 211 has its trigger input connected to a timing circuit comprising resistor 212 connected between the trigger input and the positive supply and capacitor 213 connected between the trigger input and ground. Application of power to the circuit will cause the capacitor 213 to begin to charge through the resistor 212 at a rate determined by the values of those components. When the signal increases to the trigger level of the multivibrator, a low going pulse will be produced at the $\overline{Q}$ output thereof, the width of the pulse being determined by the values of resistor 214 and capacitor 215. That low going pulse is coupled via AND gate 216 to the reset input of A/B select flip-flop 207. In addition, the low going pulse is coupled through AND gate 217 to the reset input of A memory flip-flop 218 for bringing that flip-flop back to its reset condition.

For switching from the active to the alternate supply, means are provided for changing the state of A/B select flip-flop 207, shown herein as A/B select switch 20 coupled between the positive supply of voltage and the trigger input of an A/B select monostable 219. Momentary depression of the select switch 20 triggers the monostable 219 for a period determined by resistor 220 and capacitor 221 to produce a low going pulse at the $\overline{Q}$ output which is coupled to the clock input of select flip-flop 207. It is seen that both the J and K inputs of the flip-flop 207 are coupled to the positive supply of voltage so that, with the reset circuit inactive, the receipt of a clock pulse will cause the flip-flop to toggle from its present to its alternate stable state. Thus, to switch from the A supply to the B supply or vice versa, it is simply necessary to momentarily depress the A/B select switch 20.

Figure 8:
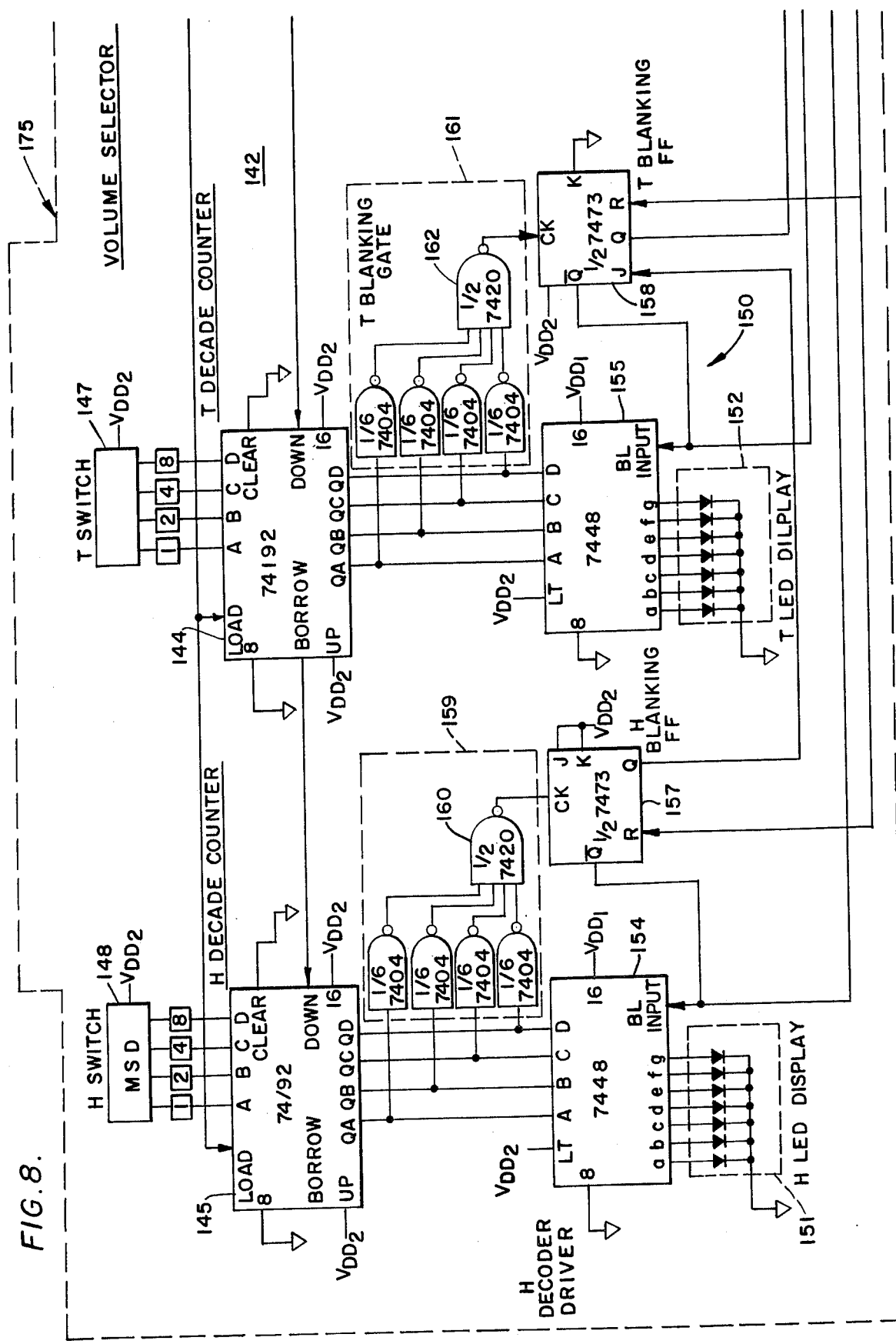
Figure 9:
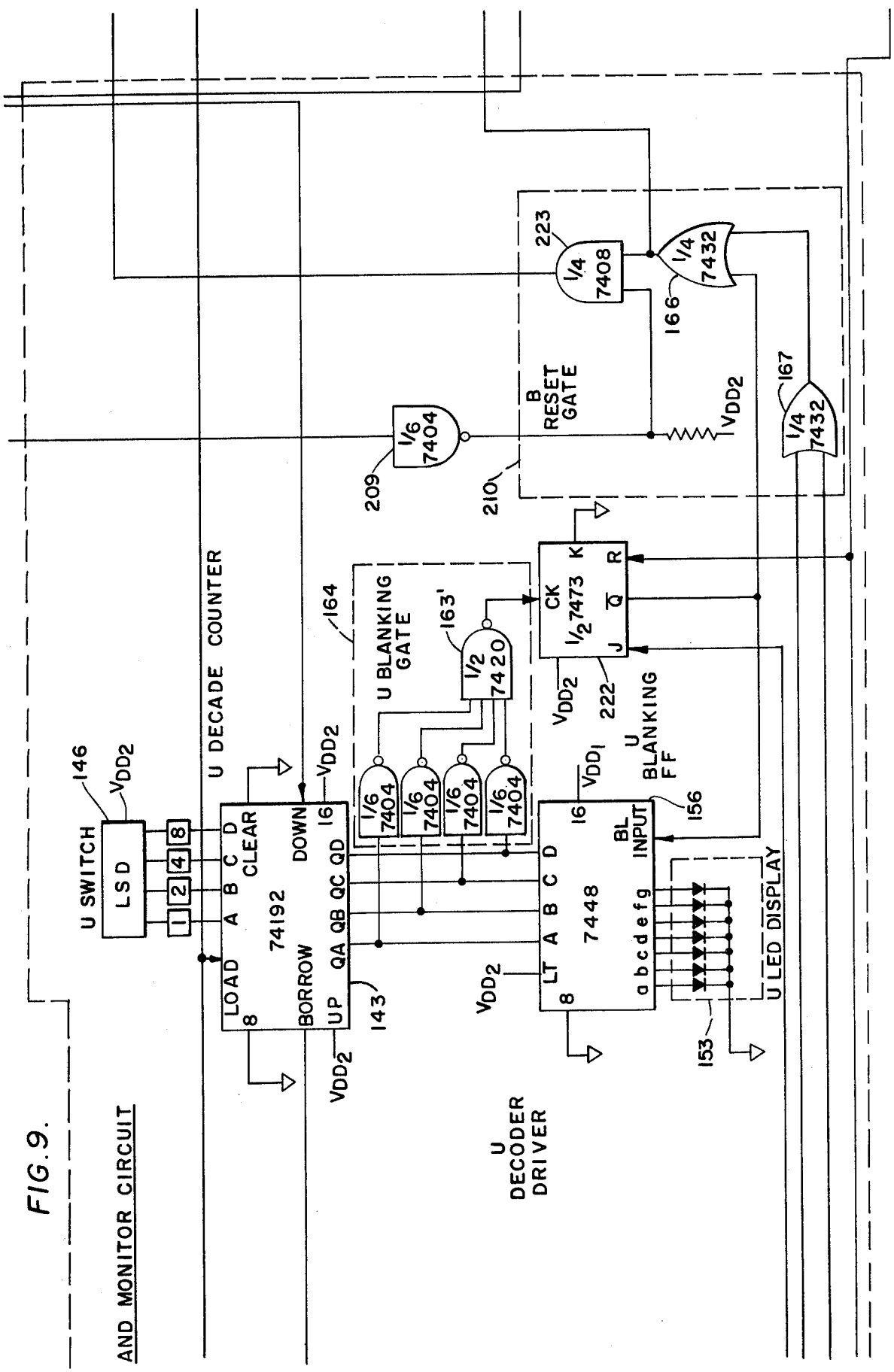

In accordance with one aspect of the invention, at least one of the supplies is provided with means for metering a predetermined volume of fluid and switching control to the alternate supply after such amount is metered. To that end, a volume selector and monitor circuit, generally indicated at 175, is provided for operation in conjunction with the A supply. As shown in FIGS. 8 and 9, such circuit includes a multi-digit counter 142, presettable to demand a given amount of fluid and preferably graduated in terms of volume, such as milliliters. The illustrated counter is constructed of three decade counter chips including units counter 143, tens counter 144 and hundreds counter 145. The counter may be preset via digital switches preferably of the thumbwheel type, including units switch 146, tens switch 147 and hundreds switch 148. It is seen that the binary outputs of the digital switches are coupled to the binary outputs of the associated counters so that provision of a strobe signal to the counter will serve to load the numbers set on the switches into the associated counter digits.

The counter is preferably arranged as a down counter, the borrow output of each digit being coupled to the down clock input of the next higher digit so that cycling of any digit downward from zero to nine will cause the next higher digit to be decremented by one. Alternatively, the counter may be arranged as an up counter appropriately gated with the volume selecting switches 146–148 so that a signal will be produced when the counter reaches the preselected amount.

For relating the number within the counter to volume of fluid dispensed, a divide by 15 counter 208 (usable with a 15 drop per milliliter drip chamber as described above) is interposed between the pulse shaper 182', 183' of the A circuit and the down clock input of the least significant digit counter 143. As a result, the divide by 15 counter 208 will respond to each drop sensed by the A drop detector 181' and, after the sensing of 15 such drops, will clock the least significant digit counter 143 to decrement the number stored within the counter 142 by one.

For displaying to an operator the progress of dispensing the predetermined volume of fluid, the selector and monitor circuit 175 includes a display, generally indicated at 150, driven by the counter 142 for showing the number remaining in the counter. In the illustrated embodiment, seven segment readouts are utilized for the display, including hundreds digit 151, tens digit 152 and units digit 153. For driving the seven segment displays, BCD to seven segment decoders 154, 155, 156 are interposed between the associated counter chips and displays. As is well known, the decoders respond to the bindary signals on their input to illuminate the proper LEDs within the seven bar display to show the numbers between zero and nine.

Readability of the display may be enhanced by including left zero blanking provided by blanking flip-flops 157, 158, 222. The most significant digit blanking flip-flop 157 has its J and K inputs tied to the positive voltage supply, and its clock driven from decoding circuitry 159 which monitors the binary outputs of the counter digit 145 to provide a low going signal at the output of NAND gate 160 when the counter 145 cycles to its zero state. Upon this occurrence, the flip-flop 157 will be clocked, changing states to drive its Q output high and $\overline{Q}$ output low. The $\overline{Q}$ output is coupled to the blanking input of decoder 154 serving to inhibit the decoder to prevent the illumination of any of the LEDs driven thereby.

The tens and units counters 144, 143 include decoding circuitry 161, 164, generally similar to that described above and having NAND gates 162, 163 for clocking the associated blanking flip-flops 158, 222. However, the J input of blanking flip-flop 158 is coupled to the Q output of blanking flip-flop 157 and the K input to ground. As a result, clock pulses will be provided to the blanking flip-flop 158 each time the tens counter 144 cycles to its zero condition. As long as a number remains within the most significant digit counter 145, the clock signal provided to flip-flop 158 will serve to maintain the Q output thereof low and the $\overline{Q}$ output thereof high, preventing the blanking of the middle digit. However, after the most significant digit counter 145 cycles to zero, the J input of flip-flop 158 is driven high, allowing the flip-flop to be clocked to its $\overline{Q}$ low state in response to the next cycle of counter 144 to its zero state.

At this time, the flip-flop 158 will apply a low signal to the blanking input of decoder 155, causing the blanking of the middle digit. The units blanking flip-flop 222 has its J input driven from the Q output of tens blanking flip-flop 158 for a similar purpose.

For monitoring the state of the counter 142 and determining when the counter is empty, B reset gate 210 is provided. In the illustrated embodiment the B reset gate includes a pair of OR gates 166, 167. The OR gate 167 has its inputs coupled to the $\overline{Q}$ outputs of the blanking flip-flops 157, 158 respectively. The output of OR gate 167 feeds the OR gate 166 which has its second input coupled to the $\overline{Q}$ output of blanking flip-flop 222. As a result, when the counter 142 is completely empty, and only then, the output of OR gate 166 will be driven low. It is seen that the output of the OR gate 166 is coupled via AND gates 223 and 216 to the reset input of A/B select flip-flop 207. As a result, when the counter is empty, the A/B select flip-flop 207 will be locked into its reset condition, automatically switching control from the A supply to the B supply. Thus, the circuitry functions not only to dispense only the preselected amount of fluid via the A supply but also reactivates the B supply at the termination of the metered cycle to switch control to the B supply for keeping the needle open.

In addition to switching control from the A to the B supply at the completion of a metered dispensing cycle, means are also provided for accomplishing such switching in the event an alarm condition is detected while functioning on the A supply. To that end, the second input of AND gate 233 is driven via inverter 209 from the output of alarm OR gate 195'. As a result, whenever the A circuit is in the alarm condition, the high signal produced by OR gate 195' will be inverted by inverter 209, and cause the output of AND gate 223 to be low, thus switching the A/B select flip-flop 207 to the reset condition, inhibiting the A supply and allowing operation of the B supply.

In the event a metered cycle on the A supply is interrupted before the completion thereof such as by sensing an alarm condition, means are provided for remembering the amount of fluid still to be dispensed so that the metered cycle may be reinitiated at the point at which it was interrupted. To that end, memory means are interposed between the A/B select monostable 219 and the load inputs of the counter 142. In the illustrated embodiment, such means include an inhibitable monostable multivibrator 224 and an A memory flip-flop 218. As shown in the drawing, the J and reset inputs of the flip-flop 218 are driven via AND gate 217 from the output of OR gate 166 so that the flip-flop is reset upon the occurrence of the counter 142 cycling to zero. The $\overline{Q}$ output of the flip-flop 218 is coupled to the B input of the monostable multivibrator 224 so as to prevent the triggering of such monostable whenever the $\overline{Q}$ output is low. Further, the A input of the monostable multivibrator 224 is coupled to the $\overline{Q}$ output of the monostable 219 so that the monostable 224 is triggered by depression of the pushbutton switch 20 if the B input is at a high level. The $\overline{Q}$ output of the monostable multivibrator 224 is coupled to the load inputs of the counter stages 143, 144, 145 so as to parallel load the numbers set on the respective thumbwheel switches 146, 147, 148 when the aforementioned $\overline{Q}$ output is driven low. In addition, the $\overline{Q}$ output of monostable 224 drives the reset inputs of blanking flip-flops 157, 158, 222 via AND gate 225, to cause the associated digits to be illuminated when the counter is loaded.

In operation, state of A memory flip-flop is controlled in part from the count within the counter 142, and in part from the A/B select monostable 219. It is recalled that when the counter 142 is empty, the output of OR gate 166 will be at a low level. That low level is passed through AND gate 217 to maintain a low signal on the reset input of A memory flip-flop 218, locking that flip-flop into its reset condition. As a result, the $\overline{Q}$ output of flip-flop 218 will apply a high signal to the inhibit input of monostable 224, allowing the monostable to respond to trigger pulses to produce an output pulse. Thus, to initiate a cycle on the A supply, it is merely necessary, having set the desired volume of fluid on the switches 146–148, to momentarily depress the select switch 20. Because the load monostable is not inhibited, the low pulse produced at the $\overline{Q}$ output of monostable 219 triggers the load monostable 224 to produce a low going pulse at the $\overline{Q}$ output thereof. The low going pulse acts upon the load inputs of counter stages 143–145, causing the number set on the digital switches to be strobed into the counter. Additionally, the low pulse produced at the $\overline{Q}$ output of monostable 244 is coupled through AND gate 225 to apply a low going pulse to the reset inputs of the blanking flip-flops 157, 158 and 222, driving each of those flip-flops to their reset condition. The $\overline{Q}$ outputs of each of the flip-flops will, therefore, be driven high, causing the output of OR gate 166 to be driven high. That high signal, coupled through AND gate 217, not only removes the reset signal from memory flip-flop 218, but additionally brings the J input thereof to a high level. At the termination of the pulse produced by select monostable 219, the Q output thereof will fall to a low level, providing a clock signal to the flip-flop 218. Because the J input is being maintained high by AND gate 217 and the K input is coupled to ground, the flip-flop 218 will respond to the clock signal by driving its Q output high and $\overline{Q}$ output low. The low $\overline{Q}$ signal is applied to the inhibit input of load monostable 224, preventing further triggering of that monostable until the counter is again emptied and the memory flip-flop 218 reset. Thus, if for any reason the cycle of the A supply is interrupted (e.g. by an alarm condition, an intended operator action, or any other reason), because both the J and reset inputs of flip-flop 218 are being maintained in the high condition, it will not be possible to change the flip-flop from its $\overline{Q}$ low condition and the load monostable 224 will continue to be inhibited. As the load monostable provides the only means for loading the counter 142, and as that load monostable is inhibited, it will be impossible to affect the number in the counter until the cycle is complete. The A/B select switch 20 will continue to act through select monostable 219 to control the A/B select flip-flop 207 and will allow switching between supplies. However, switching back to the A supply will serve to continue rather than reinitiate the cycle because the counter therein is constrained to remember the amount of fluid yet to be dispensed. After the monitor circuitry determines that the total desired amount of fluid has been dispensed, this occurrence being indicated by the counter 142 cycling to zero, the output of the B reset gate will be driven low, applying a reset signal to A/B select flip-flop 207. This action will lock the dual IV set into the B supply mode until a subsequent A supply cycle is initiated by reloading the volume selector and monitor counter 142.

In some cases it may be desirable to reset the counter 142 before the completion of a metered cycle. For example, after initiating a cycle an attendant may determine that an improper volume of fluid has been selected. To allow the counter to be reset in unusual circumstances such as these, a switch 212a is provided, and is preferably located in a partially inaccessible position, such as behind a hinged access panel or on the rear of the housing. The switch 212a shunts capacitor 213 to ground such that when the switch is momentarily depressed it discharges the capacitor. Release of the switch causes the monostable 211 to produce a resetting pulse just as when power is first applied to the circuit. It will be apparent after considering the description of the memory power supply $V_{DD2}$, that this could not be accomplished by momentarily switching the power off. The pulse produced by multivibrator 211 resets the A memory flip-flop 218 even though a count is being maintained in the counter. In addition, the pulse also resets the A/B select flip-flop 207 to return control to the B supply. The attendant may then manipulate the thumbwheel switches 146–148 to select the desired amount of fluid to be dispensed, and upon depression of the A/B select switch 20 cause the loading of the new number into the counter 142.

According to a further feature of the illustrated embodiment, the circuitry is powered from an a.c./d.c. supply so that circuit operation will continue even though the primary power source is temporarily interrupted; additionally, the circuitry is arranged so that the monitor counter 142 remembers the number stored therein, if interrupted, even though the circuitry is completely switched off. Referring to the power supply illustrated in FIG. 6, it is seen that such supply includes a line transformer 226 supplying a full wave bridge 227 in conventional fashion. A d.c. power source, such as nickel cadmium battery 228 is coupled across the output of the rectifier 227. With the ganged power switch 229 in the open condition, the battery 228 is charged via resistor 230. With the power switch 229 closed, the battery 228 is coupled directly across the supply to act as a filter when operating from a.c. However, if the source of primary power for the transformer 226 is removed, the battery 228 remains connected to the circuitry and operation continues under d.c. supply with no interruption. A power on indicator 231 may be coupled across the power supply if desired.

As a further facet of the interrupted cycle memory feature, means are provided for maintaining a memory power supply for the monitor counter 142 to allow that counter to remember the volume of fluid remaining to be delivered even if the power switch 229 is opened. It is seen that the counter stages 143–145, the A memory flip-flop 218, and certain associated components are supplied with d.c. power, not from the main power source $V_{DD1}$ but from the memory power supply $V_{DD2}$. That supply, it is seen, is derived from across the battery 228 via a set of relay contacts 232. The relay contacts 232 are controlled by a coil 233 which, in turn, is driven by a transistor 234. Base drive is provided to the transistor by a display gate 235. It is seen that one input of OR display gate 235 is connected to the main supply $V_{DD1}$ so that whenever the main supply is active, the output of OR gate 235 will be high, causing transistor 234 to conduct, energizing coil 233, closing the contacts 232 and actuating the supply $V_{DD2}$. The second input of display gate 235 is driven from the Q output of A memory flip-flop 218 which, it is recalled, is maintained at a high level as long as a count is retained within the counter 142. As a result, even if the power switch 229 is opened, if a count is being maintained in the counter 142 indicating an interrupted A cycle, the output of display gate 235 will be maintained high, causing transistor 234 to continue to conduct, maintaining the contacts 232 closed and continuing to energize the supply $V_{DD2}$ even after the supply $V_{DD1}$ has been switched off. When the attendant operates the power switch to resume operation, the circuit will commence operation with the B supply operational as described above. However, the volume of fluid remaining to be dispensed in the interrupted cycle of the A supply is remembered by the counter 142, and displayed to the attendant on the display 19 (151–153). Thus, the attendant is appraised to return control to the A supply by operation of the A/B select switch 20, so that the amount of fluid remaining will be dispensed to complete the previously initiated cycle.

Embodiment II

Turning finally to FIGS. 12–16, there is shown a further embodiment of a dual IV set, illustrating the present invention, and incorporating certain refinements over the previously described embodiment. In common with the embodiment previously described, the present dual IV set includes a B supply circuit generally indicated at 172, an A supply circuit generally indicated at 173, an A/B select circuit 174 and volume selector and monitor circuitry 175 associated with at least one of the aforementioned supply circuits. Although not illustrated in the drawings, a power supply is provided for the dual IV set including both main and memory power supplies as described in connection with Embodiment I.

It is seen that certain of the elements of Embodiment II are identical to those described above, including A/B select switch 20 driving A/B select monostable 219. The $\overline{Q}$ output of monostable 219 clocks the A/B select flip-flop 207. The Q and $\overline{Q}$ outputs of the flip-flop 207 enable one or the other of the supply circuits, but do so not by controlling the output latch as in the previous embodiment, but by controlling the delivery of clock pulses to the respective supply circuits. Additional elements identical to the previously described embodiment include the power-on reset monostable 211 for resetting the system on the initial application of power and having switch 212a coupled in its trigger circuit for manually clearing the volume counter. AND gate 216 drives the reset input of A/B select flip-flop 207 while AND gate 217 drives the J and reset inputs of memory flip-flop 218, both as described above.

According to one feature of the illustrated embodiment, a digitably settable clock 300 is provided, time shared between the A and B supply circuits for independently setting the drip rates of such supply circuits. The clock is constructed much as described in the above referenced copending application Ser. No. 637,206, the specification of which is incorporated herein by reference. As described in that application, the clock includes a time base generator in the form of astable multivibrator 301 preadjusted to a set frequency, such as 1 Hz. The output of the multivibrator 301 feeds a signal input terminal 302 of a phase locked loop 303. The second input 304 of the phase locked loop is provided at the output 305 of a two digit decade counter comprising least significant digit counter chip 306 and most significant digit counter chip 307. An operator selected number is strobed into the counter after each complete cycle thereof and, as described in the aforementioned application, adjusts the output frequency of the phase locked loop 303 (which appears at terminal 320) such that the output frequency is equal to the base frequency of the oscillator 301 multiplied by the modulus of the feedback counter 306, 307.

In contrast to the aforementioned application wherein only a single pair of digital thumbwheel switches was provided for establishing the modulus of the counter, the instant application provides two pairs of thumbwheel switches and time shares the digital clock between the A and B supply circuits at independently selected drip rates. To that end, a pair of data selectors 310, 311 are provided having outputs generally indicated at 312, 313, respectively, coupled to the data inputs of the associated counter chips 306, 307. A side thumbwheel switches 315, 316 (17A in FIG. 1) are coupled to the A selector inputs of the selectors 310, 311 while B side digital thumbwheel switches 317, 318 (17B in FIG. 1) are similarly coupled to the B selector inputs. Control inputs 319, select which set of thumbwheel data will appear at the selector outputs 312–313. When the line 319 is at a high logic level, the numbers selected on the B side thumbwheel switches 317, 318 appear at the outputs of the selectors 310, 311, so that the B side thumbwheel switches establish the frequency of the clock (which appears at terminal 320 of the phase locked loop). By way of contrast, when the selector input 319 is low, the outputs of A side switches 315, 316 are coupled by the selectors 310, 311 to the data inputs of counters 306, 307 so that the clock frequency of the phase locked loop is determined by the A side thumbwheel switches. It is seen that the output 320 of the phase locked loop, which carries the base frequency multiplied by the modulus of the counter 306, 307 as determined by the selected thumbwheel switches for the A or B side, is coupled to the clock input of time base generator 322. As described in the above referenced application, the time base generator 322 serves to divide the input signal by 60 and couple that signal as an output on terminal 323 to the remaining circuitry, such signal serving as the pulsed output for establishing the desired drip rate. In this way, the numbers displayed on the digital switches correspond directly to the drip rate in drops per minute. It is seen that the selector inputs 319 of selectors 310, 311 are driven by the $\overline{Q}$ output of A/B select flip-flop 207 so that the B supply thumbwheel switches will control the clock output when the $\overline{Q}$ output is high, enabling the B supply side.

The drip rate establishing clock signal on terminal 323 of the time base generator 322 is coupled via an interfacing driver 325 to B supply AND gate 326 and also to A supply AND gate 327. Each of such AND gates has a second input driven from the A/B select flip-flop 207, the $\overline{Q}$ output driving the enabling input of B supply AND gate 326, while the Q output drives the enabling input of A supply AND gate 327. Thus, when the $\overline{Q}$ output of the flip-flop is high, the selectors 310, 311 cause the digitally settable clock to respond to the B side thumbwheel switches, and the AND gate 326 is enabled to pass the clock pulses from driver 325 to the B supply circuit, the AND gate 327 preventing the passage of any such clock pulse. When the flip-flop 207 is in its opposite condition, the B supply is prevented from receiving clock pulses while clock pulses are coupled to the A supply circuit via AND gate 327. It will now be appreciated that the A and B supply circuits are enabled by controlling the distribution of clock pulses thereto, while the illustrated circuit uses a common clock for controlling both of such supply circuits, the common clock including separate selectors for each of the supply circuits.

The A and B supply circuits in the illustrated embodiment differ somewhat from those described in connection with Embodiment I, and provide certain additional features. The B supply circuit 172 will be described in detail, realizing that the A supply circuit is constructed in a similar fashion. It is seen that when the AND gate 326 is enabled to pass clock pulses, such clock pulses are coupled to the clock input of a retrigerable multivibrator 330 and also to the clock input of a J-K flip-flop 331. Both elements will be triggered on the negative transition of the clock, driving the respective Q outputs high and $\overline{Q}$ outputs low. It is seen that the Q outputs are coupled to the inputs of AND gate 332 so that when the multivibrator 330 and flip-flop 331 are triggered, the output of AND gate 332 will be driven high. In this condition, base drive will be provided to switching transistor 333 to cause current flow through valve coils 334, thus opening the valve in the B supply circuit.

After opening of the valve, a drop will form and fall through the drip chamber, such drop being detected by drop detector 335. The drop detector 335 is coupled to a pulse shaper 336 which, in response to detection of a drop, produces a positive pulse at the Q output thereof. A multivibrator 345 has its clock input driven from the Q output of the pulse shaper 336 and has a Q output driving transistor 346, drop indicator 347 being coupled in the load circuit thereof. As described in connection with the previous embodiment, the period of multivibrator 345 is established so that the indicator 347 is illuminated for each drop, flashing at the selected drip rate to provide an indication of proper operation.

The shaped drop pulses at the output of pulse shaper 336 are inverted by inverter 337 and coupled to the reset inputs of multivibrator 330 and flip-flop 331. Thus, when a drop is detected, both elements are reset to drive the output of AND gate 332 low, deenergizing the electromagnets 334, to close the valve. However, if no drop falls after opening of the valve, no signal will be produced by pulse shaper 336 and no reset pulse will be coupled to the elements 330, 331. At the termination of the time period established by resistor 340 and capacitor 341, the multivibrator 330 will time out, driving the output of AND gate 332 low and deenergizing the electromagnets 334. The period of multivibrator 330 is set at the maximum desired open time of the valve, such as two seconds. Since no reset signal was coupled to flip-flop 331, it will remain set, the ground connection on the K input and the interconnection between the J input and $\overline{Q}$ output, preventing the flip-flop from responding to clock pulses when in its set condition. Thus the flip-flop 331, in normal operation, is resettable only by a signal generated as a result of the detection of a drop.

The illustrated supply circuits include not only high rate and low rate alarms, but also means for accumulating high rate errors before actuating such alarms. As will become more apparent, flip-flop 350 comprises a low rate alarm flip-flop, having a $\overline{Q}$ output tied to the input of AND gate 351, such that when the flip-flop is in its set condition, the low $\overline{Q}$ output causes the output of gate 351 to switch low. This low signal is coupled to the inhibit input of multivibrator 330, preventing the multivibrator from responding to further clock pulses coupled through AND gate 326, thereby preventing further energization of the valve coil 334 or opening of the valve.

To accomplish error accumulation in the instant embodiment, the clock input of flip-flop 350 is driven by the output of a four line to one line data selector 352. In effect the data selector 352 may be considered a dual data selector, with the upper half enabled when the 1G output is low and the lower half enabled when the 2G input is low. It is seen that the 1G input is driven from the Q output of A/B select flip-flop 207 while the 2G input is driven by the $\overline{Q}$ output thereof. Thus, the upper half of the data selector is enabled when the Q output of the select flip-flop is low enabling the B side, while the lower half is enabled whenever the A side is in operation. Assuming that the upper side of selector 352 is active, the signal present on the output line 353 is selected from one of the input signals present on lines 354 through 356 in dependence on the status of the selector inputs 357, 358. The selector inputs, in turn, are driven by the most significant digit data selector 311 which, in this condition, will be passing the data set on the B supply thumbwheel switches. Gating circuitry including OR gate 359a, inverter 359b and OR gate 359c monitors the output of the most significant digit data selector for driving the selector inputs. When the most significant digit set on the thumbwheel switch 318 is 0, the output of OR gate 359a will be high, causing the output of inverter 359b to be low and the output of OR gate 359c also to be low. Thus, zeros are imposed on both inputs of the data selector 352, coupling the input line 354 to the output line 353. When the most significant digit is 1, the output of OR gate 359c will be high, while the output of inverter 359b remains low. In this condition, with selector input 357 low and selector input 358 high, the input line 355 will be coupled to the output line 353. Finally, whenever the most significant digit is 2 or larger, the outputs of both inverter 359b and OR gate 359c will be high, causing the selector 352 to couple the input line 356 to the output line 353 thereof.

A pair of flip-flops 360, 361 drive the inputs 354 through 356 of the selector, specifically the $\overline{Q}$ output of flip-flop 360 driving the input 354, the $\overline{Q}$ output of flip-flop 361 driving the input 355 and the Q output of flip-flop 361 driving the input 356. The flip-flops, in turn, have their clock inputs driven by AND gate 326 which passes clock pulses to the B supply circuit, and are adapted to be clocked by such pulses when the appropriate gates 362, 363 are enabled.

In normal operation, both AND gates 362 and 363 are disabled when a first clock pulse appears, because flip-flop 331 is in its reset condition at that time, maintaining its $\overline{Q}$ output high and, therefore, the output of inverter 364 low. It is seen that this low signal is coupled via driver 372 to an input of AND gate 362 to disable that gate, while the low Q output of flip-flop 360 disables AND gate 363. Thus, so long as operation remains normal, with clock pulses and drop pulses alternating, flip-flops 360, 361 remain static in their reset conditions. However, if no drop falls after the valve is opened, flip-flop 331 is not reset, thereby providing a high signal to the associated input of AND gate 362. Because the Q output of flip-flop 360 is low at this time, AND gate 363 will, however, remain disabled. When the next clock pulse appears with no intervening drop pulse, AND gate 362 will respond, clocking the flip-flop 360 to the set condition. If the most significant digit of the drop rate is 0, the falling $\overline{Q}$ signal will pass via input 354 of selector 352 to the output thereof, clocking the flip-flop 350 and driving its Q output high. After the $\overline{Q}$ output of multivibrator 330 falls at the termination of its predetermined period, AND gate 365 will be satisfied, producing a high signal at the output thereof and activating the alarm circuitry. It is seen that the output of AND gate 365 is coupled through OR gate 366 to illuminate the common low alarm indicator 367 and also to activate OR gate 368 to provide base drive to transistor 369, sounding the audible alarm 370. If, however, a drop is detected before the multivibrator 330 times out, the pending alarm condition will be cleared, the drop pulse appearing at the output of inverter 337 resetting the flip-flop 360 (and also 361 had it been set). Also, while the valve is open the low $\overline{Q}$ output of multivibrator 330 inverted by inverter 373 enables NAND gate 374 so that if a drop falls the NAND gate will be satisfied, coupling a low signal through AND gate 375 to reset the low rate alarm flip-flop 350. However, if no drop falls, the flip-flop 350 will remain in its set state, placing the B supply circuit into the alarm mode.

If the most significant digit of the selected drip rate for the B side is greater than 0, the circuit will not enter the alarm mode in response to the first missed drop, but will await the detection of further missed drops before doing so. The flip-flop 360 will be clocked as described above in response to the first missed drop, driving its Q output high, but the selector 352 will not pass this transition for clocking the alarm flip-flop 350. When the next clock pulse arrives, corresponding to the second missed drop, AND gate 363 will be satisfied, clocking the flip-flop 361 from its reset to its set state. The negative transition at the $\overline{Q}$ output will be coupled through the selector to the clock input of flip-flop 350 if the most significant digit of the selected drip rate is 1. Operation will be as before to enter the alarm mode. It is noted that the flip-flop 360 does not change state once it is set because the J input is tied to the $\overline{Q}$ output which is low while the K input is tied directly to ground. If the most significant digit is 2 or more, no clock signal will be passed to the flip-flop 350 in response to the second missed drop, and operation will continue. Upon receipt of the next clock pulse, corresponding to the third missed drop, the flip-flop 361 will again be clocked, returning to its reset state with a resulting negative transition appearing at the Q output thereof. If the most significant digit of the selected drip rate is 2 or greater, this negative transition will be coupled through the selector 352 to clock flip-flop 350 and cause the circuit to enter the alarm mode. Thus, at low drip rates, the circuit is very sensitive to missed drops, and will cause the alarm mode to be entered in response to the second such missed drop. However, at higher drip rates, the circuit is more tolerant, requiring three missed drops for drip rates between 10 and 19, and four missed drops for drip rates of 20 or higher.

Detection of high rate alarms is accomplished in a different manner, counting drops out of the normal sequence as they occur, and allowing the circuit to continue to function on a dispensing cycle until sufficient extra drops are counted to indicate an overall abnormal condition. To that end, a binary counter 380 is provided, presettable to a predetermined number, selected as the maximum tolerable number of extra drops, in the instant embodiment ten. As will become more apparent, at the start of the dispensing cycle, when the supply is first enabled, the parallel enter input 381 of the counter 380 is driven low, strobing the preset number 10 into the counter. The counter is arranged in the down counting mode so as to decrement the count contained thereby by one for each drop detected out of the normal sequence. It is seen that the clock input 382 is driven via AND gate 383 which has a first input maintained normally high by driver 387 and a second input driven by the positive pulses produced at the output of pulse shaper 336. The counter 380 also has an inhibit input 385 driven by the inverter 364 which responds to the $\overline{Q}$ output of the flip-flop 331. Thus, whenever the valve is open, the $\overline{Q}$ output of flip-flop 331 will be low, coupling a high signal via inverter 364 to the inhibit input of counter 380, and preventing such counter from responding to clock pulses. Thus, when the first drop falls after opening of the valve, the positive pulse produced at the output of AND gate 383 will be incapable of clocking the counter 380. However, that first pulse will reset the flip-flop 331, returning the $\overline{Q}$ output high, and coupling a low enabling signal to the input 385. If further drops fall before a subsequent valve opening clock pulse, positive pulses will be coupled through AND gate 383, clocking the counter 380 to decrement the count stored therein by one for each drop sensed. If ten extra drops are sensed over the course of a dispensing cycle, the counter 380 will be emptied, producing a low signal at output 386 thereof, such low signal being passed by driver 387. That signal is applied to one of the inputs of AND gate 383, preventing further clock pulses from being coupled to the counter 380. The low signal is also coupled to the alarm circuitry, and specifically to NAND gate 388, driving the output thereof high to illuminate the high rate alarm indicator 389. The high at the output of NAND gate 388 also causes the output of OR gate 368 to be driven high, providing base drive to transistor 369 and sounding the audible alarm 370. Finally, the low signal at the output of driver 387 is coupled to an input of AND gate 351, driving the output thereof low and presenting an inhibiting signal to multivibrator 330, preventing same from responding to further clock pulses. Thus, the system is locked into the alarm mode and further functioning disabled.

Referring now to the A supply circuit 173, it is seen that the circuit, with two exceptions, is identical to the B supply circuit 172. Accordingly, the corresponding parts have been given primed reference numerals. With regard to the differences, the outputs of low alarm gate 365' and high alarm driver 387' are monitored by gating circuitry including inverter 400 and AND gate 401 such that when either alarm is active the output of gate 401 is switched low. This low signal is coupled to one of the inputs of AND gate 402 whose output drives, via AND gate 216, the reset input of A/B select flip-flop 207. Thus, as in the previous embodiment, if an alarm condition is detected when functioning on the A supply, control is automatically switched to the B supply.

With regard to the second difference, it is seen that the drop pulses at the output of inverter 337' are coupled to the clock input of a flip-flop 405 whose $\overline{Q}$ output drives decade counter 406. The circuit is arranged as a divide by 20 counter, usable with a 20 drop per milliliter IV set so as to produce an output pulse at terminal 407 for each 20 drops sensed by the drop detector 335'. The output 407 is coupled, as in the previous embodiment, to a three stage counter 410 comprising a units counter 411, tens counter 412 and hundreds counter 413. The volume selector and monitor circuit 175 is basically as illustrated in the previous embodiment, with the exception of the gating circuitry which monitors the outputs of the counter stages. In the present instance, NOR gates 420, 421 and 422 monitor the outputs of the associated counter stages to produce a high output signal when the associated counter stage is empty. The NOR gate clocks its associated blanking flip-flop 423-425 as described previously. The $\overline{Q}$ outputs of the flip-flops are monitored in B reset gate comprising OR gates 427, 428 so that a low signal is produced at the output of OR gate 428 when the counter is completely empty. This low signal acts through AND gate 402, just as the A alarm signal, to switch control from the A supply to the B supply when the counter is empty.

Means are provided for resetting an alarm condition so that an operator, having cleared a fault condition, may resume operation on the desired supply circuit. To that end, an AND gate 430 is provided having an output driving an input of each of AND gates 375, 375'. Accordingly, whenever the output of AND gate 430 switches low, the outputs of the associated AND gates 375, 375' will be switched low, resetting both of the low alarm flip-flops 350, 350'. It is seen that the output of AND gate 430 also drives the parallel enter inputs 381, 381' of the counters 380, 380', thereby strobing the predetermined maximum number, in the instant case ten, into such counters, and clearing any high rate alarm that might have existed. The alarm reset gate 430 is operative to drive its output low in response to several conditions. Initially, an alarm reset push button 431 is provided which, when depressed by an operator, switches the output of AND gate 430 low, resetting any alarm conditions in either of the supply circuits. Secondly the AND gate 430 has an input driven from A/B select multivibrator 219 so that whenever an operator switches from one supply circuit to the other be manual depression of the switch 20, the output of AND gate 430 will be brought briefly low, clearing any alarm conditions that might have existed. Finally, gating circuitry including OR gate 432, inverter 433 and a timing circuit including resistor 434 and capacitor 435 is driven from the output of AND gate 217. Recalling that the output of AND gate 217 is switched low in two instances, namely when power is first applied to the circuit and also when the memory clear switch 212A is momentarily depressed, it is seen that in either of these conditions a brief negative pulse will be produced at the output of OR gate 432, resetting any alarm condition that might have existed.

It will now be apparent that what has been provided is an electronic control for a dual IV set including a select circuit for controlling administration of fluids at individually preselected rates from separate sources. A control circuit selectively energizes the individual supplies for operation, and switches control between the supplies under predetermined conditions. A volume selector and monitor circuit is associated with at least one of the sources so that a predetermined volume of fluid may be dispensed, the completion of a measured dispensing cycle switching control back to the alternate supply. Finally, the monitor circuitry is provided with memory means to remember the amount of fluid yet to be dispensed in an interrupted cycle to prevent an overdose of such fluid.

As this invention may be embodied in several forms without departing from the spirit or essential characteristics thereof, the present embodiment is, therefore, illustrative and not restrictive, since the scope of the invention is defined by the appended claims rather than by the description preceding them, and all changes that fall within the metes and bounds of the claims or that form their functional as well as conjointly cooperative equivalents are, therefore, intended to be embraced by those claims.

We claim:

1. A dual intravenous infusion means for use with two supplies of intravenous fluid comprising in combination, a first drip chamber adapted to be connected to one of said supplies, a second drip chamber adapted to be connected to the other of said supplies, first and second lengths of intravenous tubing respectively connected to the first and second drip chambers and forming with said drip chambers first and second fluid flow passages, first and second valve means associated with the respective passages, first and second valve operating means associated with the respective valve means, first and second drop detector means associated with the respective drip chambers for sensing drops of the intravenous fluid falling therethrough, control circuit means including first and second supply circuits connected with the valve operating means for controlling the first and second valve operating means, said control circuit means including clock means for establishing independently selectable drip rates for said first and second supply circuits, means responsive to said clock means for opening the respective valve means at the associated preselected drip rates, means responsive to said first and second drop detector means for closing the associated valve means in response to detection of a drop, alarm means responsive to variations in the actual drop rate from the preselected rate for switching the associated supply circuit into an alarm mode, said alarm means including means for terminating flow of fluid from the associated supply in said alarm mode, and selector means for selectively enabling the first or second supply circuits for independent operation, said selector means including means for switching from one supply circuit to the other.

2. The dual intravenous infusion means as set forth in claim 1, wherein the alarm means associated with at least one of said supply circuits includes means operational upon the selector means and responsive to an alarm mode in said supply circuit for switching control to the alternate supply circuit.

3. The dual intravenous infusion means as set forth in claim 1, including volume selector and monitor means associated with at least one of said fluid supplies, said volume selector and monitor means including means for preselecting an amount of fluid to be dispensed in a dispensing cycle, means responsive to the associated drop detector for measuring the amount of fluid actually dispensed, and means operational upon said selector means for switching control to the alternate supply after the preselected amount has been dispensed.

4. The dual intravenous infusion means as set forth in claim 3, further including display means for indicating the amount of fluid remaining to be dispensed in said dispensing cycle.

5. The dual intravenous infusion means as set forth in claim 3, including remembering means actuated in the event a dispensing cycle is interrupted for remembering the amount of fluid remaining to be dispensed in said cycle.

6. The dual intravenous infusion means as set forth in claim 3, wherein the volume selector and monitor means comprises a counter, switch means operational upon said counter for selecting a volume of fluid to be dispensed, means for loading said counter with the volume selected by said switch means to initiate a dispensing cycle, and means for detecting a count remaining in said counter and inhibiting said loading means in response thereto, thereby to remember the number within the counter in the event said dispensing cycle is interrupted.

7. The dual intravenous infusion means as set forth in claim 6, including primary power supply means for supplying power to said dual intravenous infusion means, memory power supply means for supplying power to said counter, and means responsive to the presence of a count remaining in said counter for actuating said memory power supply means, whereby the volume remaining to be dispensed is remembered even if the primary power supply means is removed.

8. A dual intravenous infusion means for use with two sources of intravenous fluid, comprising in combination: first and second individual intravenous infusion sets, each set comprising a drip chamber adapted to be connected to one of said fluid supplies, a length of intravenous tubing connected to the drip chamber and forming with said drip chamber a fluid flow passage, valve means associated with the fluid flow passage, valve operating means associated with the valve means, drop detector means associated with the drip chamber for sensing drops of intravenous fluid falling therethrough, and supply circuit means; said supply circuit means including clock means for establishing an independently selectable drip rate for said supply circuit, means responsive to said clock means for opening the respective valve means at the preselected drip rate, means responsive to said drop detector means for closing the valve means in response to detection of a drop, alarm means responsive to variations in the actual drop rate from the preselected drop rate for switching the supply circuit into an alarm mode, said alarm means including means for terminating flow of fluid in said alarm mode; and selector means for selectively enabling the first or second supply circuit for independent operation, said selector means including means for switching from one supply circuit to the other.

9. The dual intravenous infusion means as set forth in claim 8, wherein the selector means includes bistable means having first and second stable states, said bistable means being coupled to said first and second supply circuits for allowing operation of said first supply circuit in said first stable state and said second supply circuit in said second stable state.

10. The dual intravenous infusion means as set forth in claim 9, wherein each valve means has an open position and a closed position, and includes a lifting magnet for opening said valve under the control of said supply circuit, and a hold down magnet for holding said valve in the closed position, said bistable means being coupled to said hold down magnets for energizing the hold down magnet associated with the valve means in the second supply circuit when the bistable means is in said first stable state, and for energizing the hold down magnet associated with the valve means in the first supply circuit when the bistable means is in said second stable state, whereby backflow through the non-operating set is prevented.

11. The dual intravenous infusion means as set forth in claim 8, wherein the alarm means of at least one of said supply circuits includes means operational upon the selector means and responsive to an alarm mode in said supply circuit for switching control to the alternate supply circuit.

12. The dual intravenous infusion means as set forth in claim 8, including volume selector and monitor means associated with at least one of said supply circuits, said volume selector and monitor means including means for preselecting an amount of fluid to be dispensed in a dispensing cycle, means responsive to the associated drop detector for measuring the amount of fluid actually dispensed, and means operational upon said selector means for switching control to the alternate supply circuit after the preselected amount has been dispensed.

13. The dual intravenous infusion means as set forth in claim 12, further including display means for indicating the amount of fluid remaining to be dispensed in said dispensing cycle.

14. The dual intravenous infusion means as set forth in claim 12, including remembering means actuated in the event a dispensing cycle is interrupted for remembering the amount of fluid remaining to be dispensed in said cycle.

15. The dual intravenous infusion means as set forth in claim 12, wherein the volume selector and monitor means comprises a counter, manually operable switch means operational upon said counter for selecting a volume of fluid to be dispensed, means for loading said counter with the volume selected by said switch means to initiate a dispensing cycle, and means for detecting a count remaining in said counter and inhibiting said loading means in response thereto, thereby to remember the number within the counter in the event said dispensing cycle is interrupted.

16. The dual intravenous infusion means as set forth in claim 15, including primary power supply means for supplying power to said intravenous infusion sets, memory power supply means for supplying power to said counter, and means responsive to the presence of a count remaining in said counter for retaining said memory power supply, whereby the volume remaining to be dispensed is remembered even if the primary power supply is removed.

17. A dual intravenous infusion means for controlling the dispensing of intravenous fluid from first and second sources of intravenous fluid comprising in combination, first and second fluid flow passages connected to the respective fluid sources, first and second valve means associated with the respective fluid flow passages for controlling flow therethrough, first and second valve control means connected with the respective valve means for opening and closing the respective valve means at individually selectable rates, and selector means connected with the control means for selectively enabling each valve means to individually deliver fluid from its associated fluid source at the rate selected therefor, said selector means including means for switching control between the first and second valve control means, at least one of said valve control means including alarm means for detecting deviations between the actual rate of delivery of said fluid and the selected rate and in response thereto putting the associated valve control means into an alarm condition, said alarm means being coupled to said selector means for switching control to the alternate control means in response to an alarm condition.

18. The dual intravenous infusion means as set forth in claim 17, further including volume selector and monitor means associated with at least one of said valve control means, said volume selector and monitor means including means for preselecting an amount of fluid to be dispensed in a dispensing cycle of the associated fluid passage, means for monitoring the amount of fluid actually dispensed during said cycle, and means for switching control to the alternate valve control means after the preselected amount of fluid has been dispensed through one of said valve means.

19. The intravenous infusion means as set forth in claim 18, including means operational in conjunction with said monitoring means for remembering the amount of said preselected volume still to be dispensed in the event a dispensing cycle is interrupted.

20. The dual intravenous infusion means as set forth in claim 18, further including display means operative in response to the amount of fluid dispensed for indicating the amount of fluid remaining to be dispensed in said cycle.

21. The dual intravenous infusion means as set forth in claim 18, including means for interrupting a dispensing cycle, means for remembering the amount of fluid not yet dispensed upon the interruption of said cycle, and means for resuming the interrupted dispensing cycle to dispense only the portion of the preselected amount not dispensed prior to the interruption.

22. Control means for use with multiple intravenous infusion sets, wherein the infusion sets each includes a fluid flow passage means adapted to be connected with a source of intravenous fluid, and valve means in the fluid flow passage means operational between an open position and a closed position to control flow therethrough, said control means comprising valve operating means for opening the respective valve means, digitally settable clock means for preselecting the rate of operation of the valve operating means and thus for selecting the rate of the valve opening and rate of flow therethrough, counter means for counting the amount of fluid dispensed, selector means for selectively enabling operation of the respective valve operating means, said selector means including means for disabling one valve operating means and enabling the other in response to the occurrence of a predetermined condition, said selector means further including means which functions when returning to an interrupted cycle to prevent the counter means from beginning a new count, whereby the counter means remembers the amount of fluid dispensed and continues the count of the interrupted cycle, supply circuit means connected with each valve operating means to control operation thereof, said digitally settable clock means connected with said supply circuit means to effect actuation thereof to obtain a desired drip rate, said clock means being shared by the supply circuit means, and alarm means for giving an alarm when the drip rate actually delivered differs by a predetermined amount from that set, and including high rate error accumulating means which counts extra drops over a dispensing cycle and goes into alarm when a predetermined number of excess drop signals are accumulated.

23. A multiple intravenous infusion means for independently and consecutively controlling flow of separate intravenous fluids through a plurality of intravenous infusion sets, including: a plurality of intravenous infusion sets; valve means associated with each set; valve operating means for opening and closing each valve means at a preselected rate; selector means for enabling one valve operating means and disabling the other; and alarm means associated with at least one of said valve operating means for detecting deviations between the actual rate of delivery of fluid and the selected rate and operative in response to a deviation to operate said selector means to disable the valve operating means associated with the alarm condition and to enable the alternate valve operating means, whereby in the event of an alarm condition occurring in one of the sets, intravenous fluid automatically continues to be supplied through another set.

* * * * *